(12) United States Patent
Ito

(10) Patent No.: US 6,379,973 B1
(45) Date of Patent: Apr. 30, 2002

(54) CHROMATOGRAPHIC SEPARATION APPARATUS AND METHOD

(75) Inventor: Yochiro Ito, Bethesda, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/263,609

(22) Filed: Mar. 5, 1999

(51) Int. Cl.$^7$ .................... G01N 1/18; B01D 11/00
(52) U.S. Cl. ............. 436/178; 210/85; 210/321.84; 210/511; 210/634; 210/702; 209/1; 209/155; 422/69
(58) Field of Search ................ 210/85, 321.83, 210/321.84, 321.85, 321.87, 511, 634, 639, 644, 649, 650, 739, 512.1, 638, 787, 148, 702; 435/4, 287.1, 6; 422/69, 72; 436/178; 209/1, 15.5

(56) References Cited

U.S. PATENT DOCUMENTS

| | | | |
|---|---|---|---|
| 2,986,280 A | 5/1961 | Magnuson et al. ...... 210/198.2 |
| 3,065,148 A | * 11/1962 | Ferrari ................. 210/321.85 |
| 3,352,422 A | * 11/1967 | Heden .................. 210/321.85 |
| 3,399,972 A | 9/1968 | Skeggs et al. ............ 23/230 |
| 3,617,557 A | 11/1971 | Giltrow | |
| RE27,806 E | 10/1973 | Dienst et al. ............. 260/112 |
| 3,840,121 A | 10/1974 | Baram | |
| 3,856,669 A | 12/1974 | Ito et al. ................ 210/198.2 |
| 4,147,621 A | 4/1979 | Giddings .................. 210/748 |
| 4,321,138 A | 3/1982 | Ito ........................ 210/198.2 |
| 4,322,275 A | * 3/1982 | Jain | |
| 4,351,710 A | * 9/1982 | Jain | |
| 4,425,112 A | 1/1984 | Ito ............................. 494/18 |
| 4,551,251 A | 11/1985 | Kolobow et al. ............. 210/635 |
| 4,623,470 A | 11/1986 | Adler ......................... 210/787 |
| 4,628,204 A | 12/1986 | Maes ........................... 250/343 |
| 4,652,364 A | 3/1987 | Shirato et al. ................ 210/87 |
| 4,741,832 A | 5/1988 | Leonard ...................... 210/638 |
| 4,775,476 A | 10/1988 | Melcher et al. ............. 210/635 |
| 4,789,468 A | * 12/1988 | Sirkar .......................... 210/137 |
| 4,794,088 A | 12/1988 | Miyaki et al. ............... 436/161 |
| 4,874,507 A | 10/1989 | Whitlock ...................... 209/11 |
| 4,894,146 A | 1/1990 | Giddings ...................... 209/12 |
| 4,968,428 A | 11/1990 | Nunogaki ................... 210/635 |
| 5,160,625 A | 11/1992 | Jonsson et al. ............. 210/635 |
| 5,366,622 A | 11/1994 | Geyer .......................... 210/199 |
| 5,434,079 A | 7/1995 | Mozayeni .................... 435/311 |
| 5,442,175 A | 8/1995 | Dawson ....................... 250/288 |
| 5,468,847 A | 11/1995 | Heilmann et al. ............ 530/413 |
| 5,578,204 A | 11/1996 | Bartholmes et al. ..... 210/198.2 |
| 5,595,650 A | 1/1997 | Manz ....................... 210/198.2 |
| 5,679,231 A | * 10/1997 | Alexander et al. ..... 210/321.87 |
| 5,932,100 A | * 8/1999 | Yager et al. ................. 210/511 |
| 5,961,832 A | * 10/1999 | Shaw et al. ................. 210/634 |

FOREIGN PATENT DOCUMENTS

| | | |
|---|---|---|
| WO | WO 97/31692 | 9/1997 |
| WO | SO-97/39338 | 10/1997 |

OTHER PUBLICATIONS

Analytical Chemistry, Kellner, Et al., editors, Wiley, 1998, Section 5.6, Field Flow Fractionation.

* cited by examiner

Primary Examiner—Joseph W. Drodge
(74) Attorney, Agent, or Firm—Knobbe, Martens, Olson & Bear, LLP

(57) ABSTRACT

A fractionation apparatus comprises two channels coupled through a semipermeable membrane. A time and position dependent concentration of precipitation reagent is produced in one of the channels. Sample entities such as macromolecules or cells introduced into this channel are eluted therefrom at different times depending on their solubility or mobility in the presence of the precipitation reagent.

28 Claims, 19 Drawing Sheets

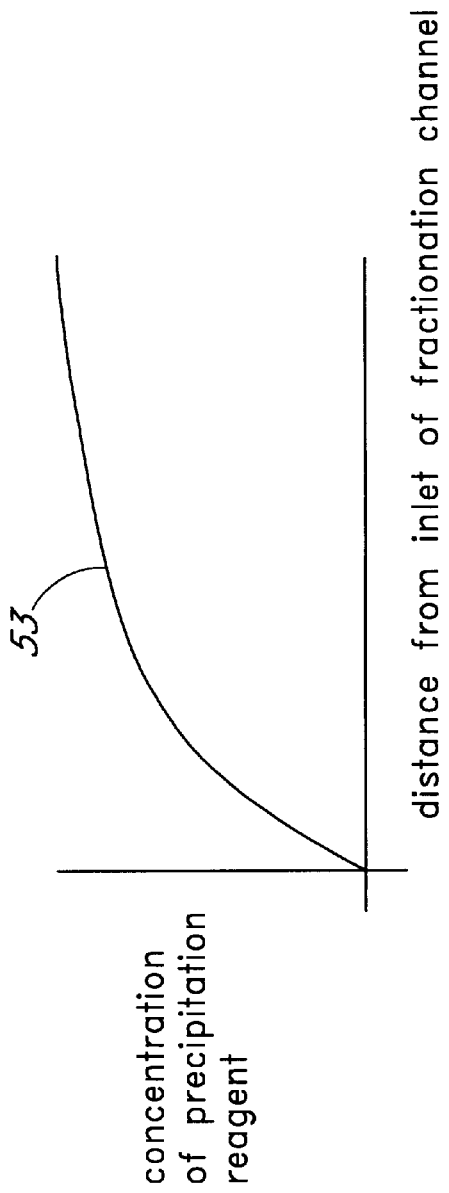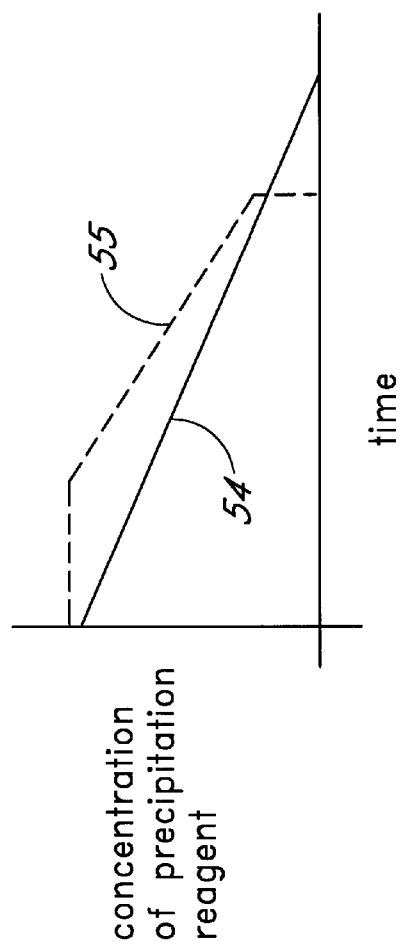
FIG. 3A
FIG. 3B

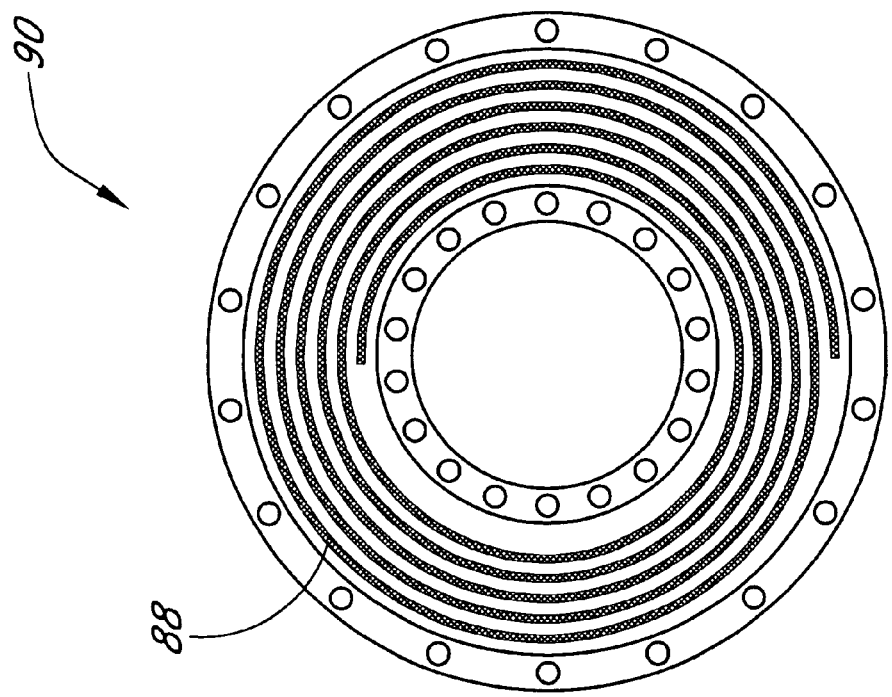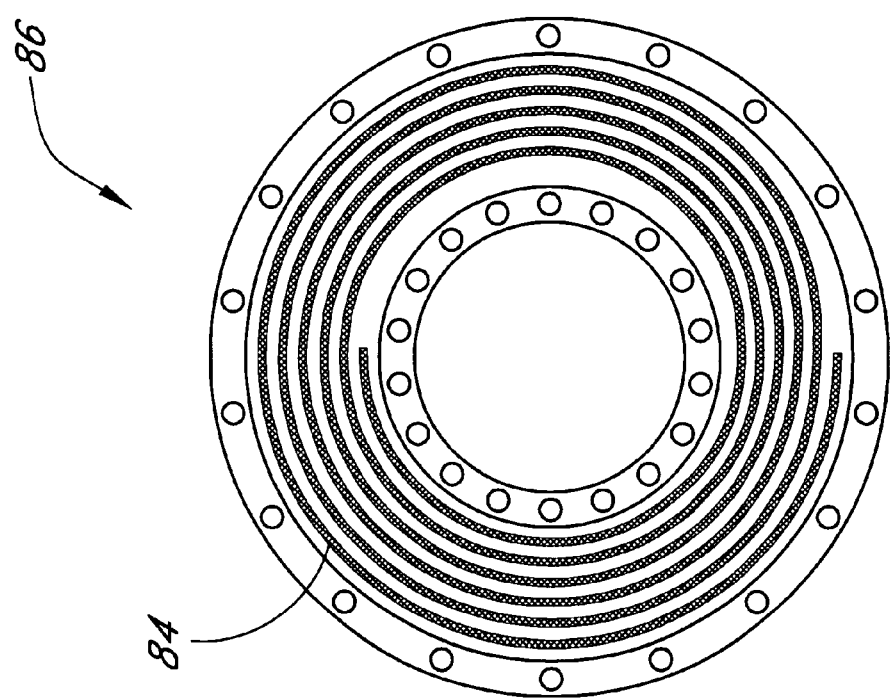
FIG. 5

CHROMATOGRAPHIC SEPARATION APPARATUS AND METHOD

BACKGROUND OF THE INVENTION

1. Field of the Invention

The invention relates to fractionation apparatus and methods, and finds especially advantageous application to the separation of biological macromolecules.

2. Description of the Related Art

The separation and purification of biological macromolecules is an important aspect of biochemical research and pharmaceutical development. Accordingly, a wide variety of procedures have been developed to isolate desired molecular species from a crude sample of biological material such as a cell lysate. These methods include electrophoresis, elution through a chromatography column, field-flow fractionation, and sequential precipitation techniques, to name a few. In most instances, performing a series of several different separation steps is required in the process of isolating a desired molecule from an initial sample of raw biological material.

Among the various separation protocols mentioned above, the sequential precipitation techniques are both commonly performed and labor intensive. One specific precipitation technique, ammonium sulfate precipitation, has been estimated to be part of approximately 80% of the currently developed protein purification protocols. In this technique, purification is performed by sequentially precipitating sample fractions in solutions having either a progressively higher or a progressively lower concentration of ammonium sulfate. This process requires a large amount of tedious manual preparation of ammonium sulfate solutions as well as manual fraction collection and re-precipitation.

Thus, in contrast with many other molecular separation techniques which may be relatively highly automated, precipitation based separation methods remain labor intensive and highly time consuming.

SUMMARY OF THE INVENTION

The invention provides a significant increase in the speed and efficiency of precipitation based fractionation apparatus and methods. In one embodiment, the invention comprises a channel having therein a solution of a precipitation reagent, wherein the concentration of the precipitation reagent is different at a first position in the channel than at a second position in the channel. The concentration at any given point in the channel may be reduced or increased as a function of time.

The apparatus may take a variety of forms. In one embodiment, the apparatus comprises a first channel containing a precipitation reagent, a second channel containing a sample for fractionation, and a semi-permeable membrane separating the first channel from the second channel.

Methods of separating target entities are also provided. In one embodiment, such a method comprises varying a concentration of a precipitation reagent from a first end of a channel to a second end of a channel, introducing a sample into the first end of the channel, and eluting the sample from the second end of the channel.

BRIEF DESCRIPTION OF THE DRAWINGS

FIG. 3A is a graphical representation of the concentration of precipitation reagent as a function of position that is advantageously produced in the sample channel of FIGS. 1 and 2.

FIG. 3B is a graphical representation of the concentration of precipitation reagent as a function of time at a given position that is advantageously produced in the sample channels of FIGS. 1 and 2.

FIG. 5 is a top view of a pair of disks having mating spiral channels formed therein that may be used to form the dual channel fractionation apparatus of FIG. 3.

DETAILED DESCRIPTION OF THE INVENTION

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
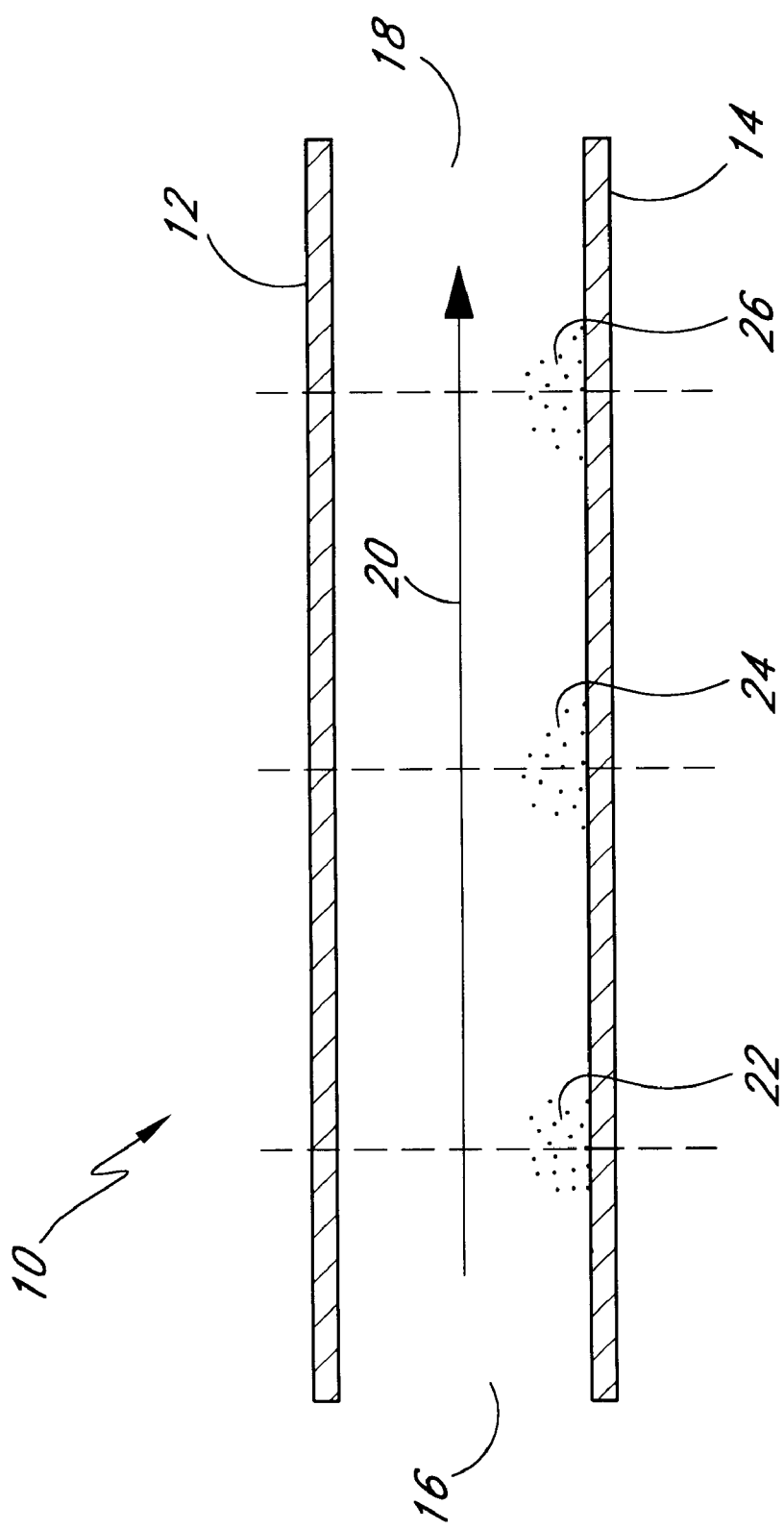
FIG. 1 is a cross section of a fractionation channel according to one embodiment of the invention.

Referring now to FIG. 1, a flow channel 10 is illustrated, having a fluid confined between an upper wall 12 and a lower wall 14. The channel 10 additionally comprises an inlet 16 and an outlet 18, allowing fluid flow in a rightward direction as indicated by arrow 20 in FIG. 1. In one advantageous embodiment, the channel 10 of FIG. 1 comprises a fractionation channel for separating and purifying biological macromolecules. Samples to be fractionated are introduced into the channel via the inlet 16, flow slowly through the channel 10 in the direction of the arrow 20, and fractions are sequentially collected at the outlet 18.

Sample fractionation is advantageously performed by the presence of a precipitation reagent in the channel 10 that varies in concentration at different locations in the channel. In the embodiment illustrated in FIG. 1, the concentration of precipitation reagent changes essentially continuously from the inlet 16 to the outlet 18. As will be explained in detail below, this variable concentration of precipitation reagent results in a separation of molecular species along the channel 10 as the sample flows from the inlet 16 to the outlet 18.

As used herein, a precipitation reagent is any substance that renders a target entity either more or less soluble or mobile in the solvent contained in the channel. In some specific embodiments described below, an increase in the concentration of a precipitation reagent results in a decrease in the solubility in the channel solvent of one or more target species which are present in the sample to be fractionated. In other embodiments, an increase in the concentration of precipitation reagent increases the mobility of a target entity within the channel. In one embodiment described in detail herein, the precipitation reagent is ammonium sulfate, and the solvent in the channel 10 is water. Additional possibilities include sodium chloride or polyethylene glycols. A further alternative precipitation reagent for an aqueous channel solvent is any acid or base. This may create a pH gradient along the channel 10, and may be especially applicable to DNA and RNA fractionation. Non-aqueous channel solvent systems are also possible. For example, the channel solvent may comprise alcohol, and the precipitation reagent may be ether or hexane for example. This system may be advantageous for isolating a molecular species that is soluble in alcohol, but insoluble in a less polar solvent. A further alternative precipitation reagent, also described in more detail below, is a high molecular weight polymer such as hydroxyethyl starch, dextran, ficoll, gum arabic, albumin, as well as others. Varying concentrations of polymer can produce a density gradient along the channel 10, which can be especially advantageous in cell separation applications. The most advantageous choice of solvent and precipitation reagent will of course depend on the nature of the target molecule or entity and the other sample substances from which the target is to be isolated.

As mentioned above, a significant effect of the position dependent concentration of precipitation reagent in the channel 10 is that different entities that have different solubilities or mobilities in the presence of the precipitation reagent will precipitate or sediment out of the solvent at different locations within the channel 10. For example, a given sample introduced into the channel 10 may comprise three different protein species. A first protein may precipitate out of solution at an ammonium sulfate concentration of anything over 20% saturated. A second protein may precipitate out of solution at an ammonium sulfate concentration of anything over 40% saturated. A third protein may precipitate out of solution at an ammonium sulfate concentration of anything over 80%. If the concentration of ammonium sulfate increases from approximately 0% at the inlet 16, to approximately 100% saturated at the outlet 18, the first protein may be predominantly retained in the channel at approximately location 22 near the inlet 16, where the ammonium sulfate concentration passes through 20% saturated. Similarly, the second protein may be predominantly retained at approximately location 24, where the ammonium sulfate concentration passes through 40% saturated. The third protein may be predominantly retained at approximately location 26, where the ammonium sulfate concentration passes through 80% saturated. Thus, the three proteins are isolated from one another by the channel 10 of FIG. 1 using ammonium sulfate precipitation without the time consuming manual methods of the prior art.

Figure 2:
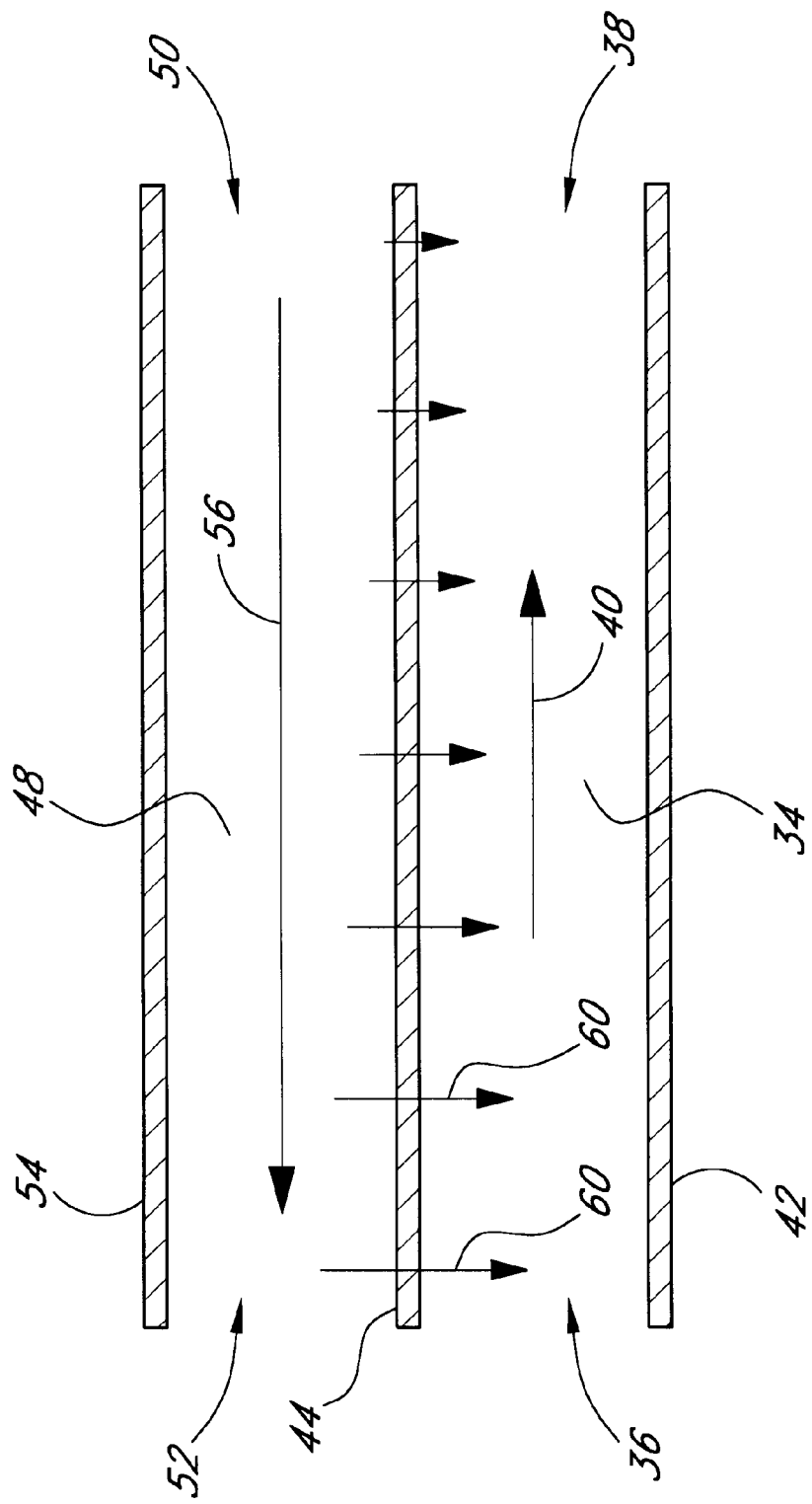
FIG. 2 is a cross section of a dual channel fractionation apparatus that may be used to produce a position dependent concentration of precipitation reagent in the channel of FIG. 1.

FIG. 2 illustrates one advantageous method of forming the channel 10 of FIG. 1, with its above described position dependent concentration of precipitation reagent. In this embodiment, a fractionation channel 34 has an inlet 36 and an outlet 38, with fluid flow moving from left to right as indicated by the arrow 40 in FIG. 2. This channel is bounded on one side by a first wall 42, and on another side by a partition 44 which separates the fractionation channel 34 from a second channel 48. The second channel 48 includes an inlet 50 and an outlet 52, and is bounded on the other side by another channel wall 54. Fluid flow in the second channel 48 is advantageously from right to left in FIG. 2, as indicated by the arrow 56, which is opposite to the direction of fluid flow in the fractionation channel.

A position dependent precipitation reagent concentration is created in the fractionation channel 34 by using a semi-permeable membrane for the partition 44, and by introducing a solution of the desired precipitation reagent into the second channel 48, which will be therefore referred to herein as the precipitation reagent channel 48. The precipitation reagent flows through the semi-permeable membrane 44 from the precipitation reagent channel 48 to the fractionation channel 34, as indicated by the arrows 60 of FIG. 2. The mass flow rate of precipitation reagent through the membrane 44 will be approximately proportional to the difference in precipitation reagent concentration at every point along the interface between the two channels 34, 48. In the general case, a steady state will be reached. If the fluid introduced into the inlet 36 of the fractionation channel 34 is free of precipitation reagent, a steady state concentration of precipitation reagent will be formed in the fractionation channel 34 which increases substantially continuously from the inlet end 36 to the outlet end 38. In addition, as precipitation reagent moves from the precipitation reagent channel 48 to the fractionation channel 34, the concentration of precipitation reagent in the second channel 48 will decrease substantially continuously from its inlet end 50 to its outlet end 52.

In one advantageous embodiment, the flow rate of the solution of precipitation reagent through the precipitation channel 48 is much greater than the flow rate of the fluid flowing through the fractionation channel 34. In this case, the concentration of precipitation reagent in the channel 48 remains approximately constant throughout its entire length because the rate that precipitation reagent is lost to the fractionation channel 34 is much lower than the rate at which precipitation reagent is introduced into the precipitation reagent channel 48.

FIG. 3A illustrates the approximate concentration of precipitation reagent in the fractionation channel 34 when the flow rate of fluid in the second channel 48 is much higher than that in the fractionation channel 34. At the inlet end 36 of the fractionation channel 34, the concentration of precipitation reagent is essentially zero, as the fluid entering the inlet is free of precipitation reagent. The concentration rises relatively quickly away from the inlet end 36, however, because the concentration difference between the second channel 48 and the fractionation channel 34 is highest at this end. Moving further toward the outlet end 38 of the channel 34, the concentration of precipitation reagent in the fractionation channel 34 rises, and thus the mass flow rate from the second channel 48 decreases, as indicated by the progressively shortened arrows 60 of FIG. 2. This produces a continuously increasing precipitation reagent concentration along the channel length. If the flow rate is constant along the channel, the concentration of precipitation reagent will theoretically follow a functional dependence upon distance from the inlet 36 of the form $C(1-e^{-kx})$, wherein C and k are constants, and wherein x is the distance from the inlet end of the fractionation channel 34. This is the functional form represented by the solid line 53 of FIG. 3A. In this formula, C is the approximately position independent concentration of precipitation reagent in the second channel 48, and k is a transfer rate constant which will be dependent on the characteristics (such as pore size and density, thickness, etc.) of the membrane 44. The actual position dependence of precipitation reagent concentration in the fractionation channel likely deviates from this exponential form due to the fact that migration of water across the membrane results in a reduction of flow rate along the fractionation channel. However, the concentration will typically approximate this exponential dependence.

As described above, such a gradient of precipitation reagent concentration in the fractionation channel 34 causes position dependent precipitation of molecular species to occur along the length of the channel 34. In advantageous embodiments, some of which are described in more detail below, a centrifugal force field transverse to the flow directions indicated by arrows 40, 56 in FIG. 2 is utilized to retain these precipitated fractions against one of the channel walls. Thus, when a sample containing molecular species to be separated is introduced into the inlet 36, different species having different solubility in the precipitation reagent are separated and isolated from one another along the channel 34 length.

Once separated along the channel length, these separated fractions may be eluted from the outlet end 38 of the fractionation channel 34 by timewise reduction in precipitation reagent concentration along the entire length of the fractionation channel 34. This may be accomplished by a timewise reduction in the concentration of precipitation reagent introduced into the precipitation reagent channel 48. This is illustrated in the graph of FIG. 3B, which represents the concentration of precipitation reagent in the fluid introduced into the inlet 50 of the precipitation reagent channel 48 as a function of time. This reduction may be performed in a variety of manners. In one embodiment, illustrated by the solid line 54 in FIG. 3B, the reduction may be a substantially linear continuous drop in precipitation reagent concentration. In another embodiment, illustrated by the dashed line 55 in FIG. 3B, the concentration of precipitation reagent may be held constant for a period, then linearly reduced to a second level, and then relatively abruptly dropped to essentially zero.

It will be appreicated that this drop in precipitation reagent concentration in the fluid introduced into the channel 48 will produce a similar time dependent reduction of the concentration of precipitation reagent at any given point along the length of the fractionation channel 34. Although the concentration of precipitation reagent at any chosen location of the fractionation channel is decreasing, the position dependence of the concentration remains unchanged. Therefore, the increasing concentration gradient from the inlet 36 to the outlet 38 of the fractionation channel 34 is maintained over time, at least until no more precipitation reagent is being introduced into the precipitation reagent channel 48, and both channels 34, 48 have been flushed with clean solvent.

This has the advantageous effect that as the concentration of precipitation reagent is proportionally decreased in the fractionation channel 34, a molecular species precipitated at a given location will be dissolved and reprecipitated at a point slightly farther down the channel toward the oulet end 38. This dissolving, downward travel, and reprecipitation will occur repetitively as a given molecular species travels down the channel 34 until eluted at the outlet end 38 when the highest concentration of precipitation reagent in the fractionation channel 34 becomes too low to precpitate that species from the solvent. Thus, the molecular species introduced into the fractionation channel 34 are eluted in the order of their solubility in the presence of the precipitation reagent.

Figure 4:
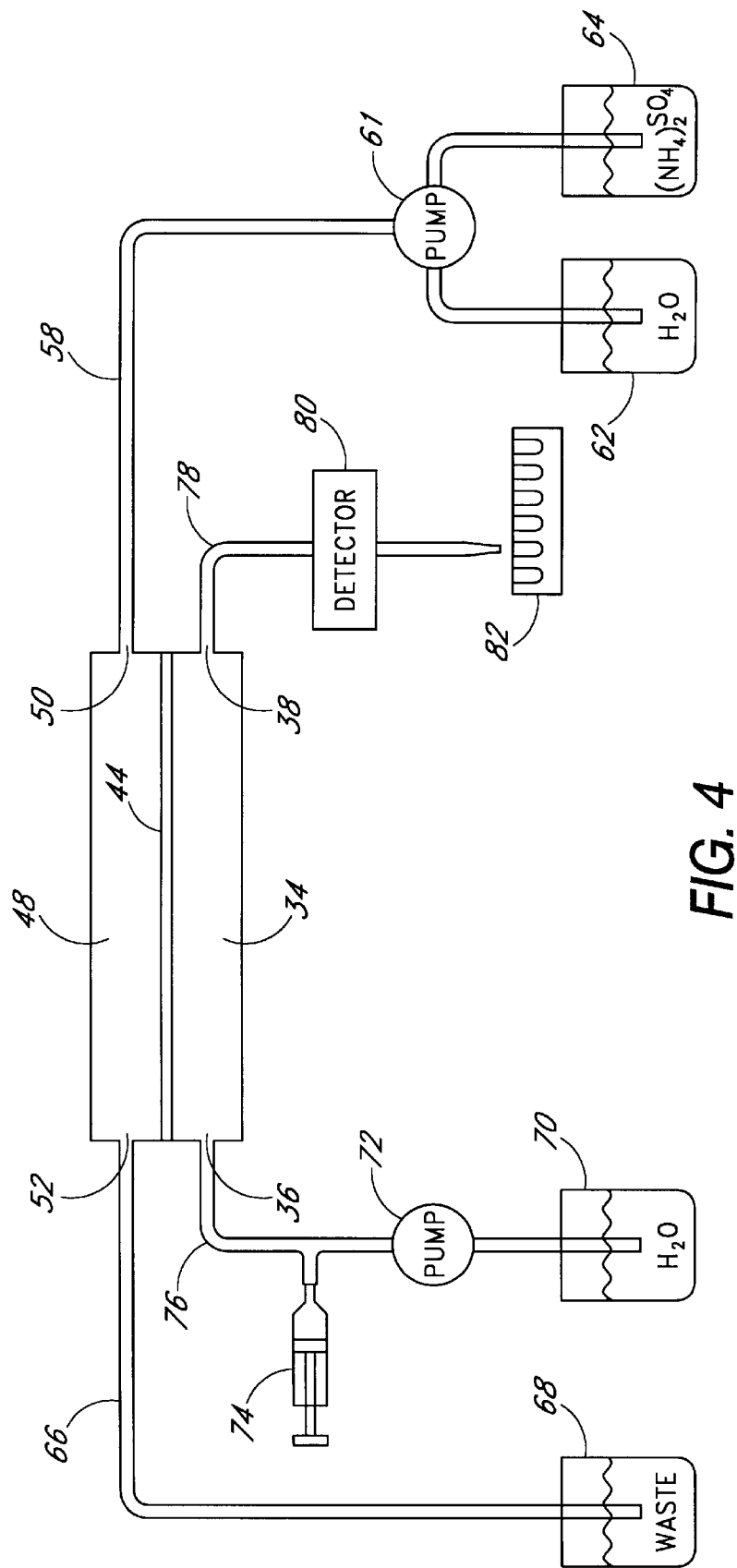
FIG. 4 is an overall block diagram of a fractionation apparatus according to one embodiment of the invention.

FIG. 4 illustrates a fractionation system embodiment which incorporates the dual channel structure illustrated in FIG. 2. As in FIG. 2, the system of FIG. 4 includes a fractionation channel 34 having an inlet 36 and an outlet 38, as well as a precipitation reagent channel 48 having an inlet 50 and an outlet 52. The two channels are separated by a semi-permeable membrane 44. The inlet of the precipitation reagent channel 48 is fed via a feed line 58 by a gradient pump 61. Suitable gradient pumps for use with the invention are commercially available from, for example, Perkin Elmer of Norwalk, CT as their model 200 series. The gradient pump 60 is coupled to two sources. One is a solvent solution 62, and the other is a solution of precipitation reagent 64. As shown in FIG. 4, the solvent may be water, and the precipitation reagent may be a saturated solution of ammonium sulfate. As described above, the solvent and precipitation reagent may vary widely, and may be water and a precipitating salt, water and an acid or base, miscible organic substances such as alcohol and ether, etc. The gradient pump outputs a programmable mixture of solvent and precipitation reagent into the feed line 58. This pump 60 may advantageously be programmed such that the proportion of the output of the pump 60 coming from the source of precipitation reagent 64 steadily decreases. This may produce the time varying concentration of precipitation reagent illustrated in FIG. 3B. The outlet 52 of the precipitation reagent channel is coupled with another fluid line 66 to a waste container 68.

The inlet 36 of the fractionation channel 34 is fed by a source of solvent 70, which may be, for example, water. The solvent source 70 is coupled to a pump 72 which forces the solvent through the fractionation channel 34. In one embodiment, this pump is a commerically available syringe pump from, for example, Harvard Apparatus of Southnatick, Mass. Another syringe 74 may be used to inject samples to be fractionated into the fluid line 76 which feeds the inlet 36 of the fractionation channel 34. The outlet 38 of the fractionation channel feeds a fourth fluid line 78 that may be coupled to an appropriate detector 80. For protein fractionation, the detector may continuously measure the UV absorbance of the eluate as it is pumped through the channel 34. A suitable instrument is manufactured commercially by LKB Instruments in Stockholm, Sweden as the model Uvicord S, for instance. Of course, the nature of the detector 80 will vary depending on the nature of the molecular species being detected in the eluate.

Following detection, a multi-well fraction collector 82 may be utilized to separate fractions of the eluate. In pharmaceutical production applications of the invention, one or more fractions may be incorporated into a medicament, diagnostic kit, or other medical or pharmaceutical product. In applications involving biochemical research, the various fractions of eluate may be for collected for further evaluation with, for example, activity testing, electrophoretic analysis, or other analysis and characterization methods.

As mentioned above, it is advantageous to form a centrifugal force field in the channels 34, 48 transverse to the direction of flow through them. It is accordingly advantageous to form the channels 34 and 48 into a spiral or helical configuration so that they may be rotated around a common axis to produce the desired transverse centrifugal force. In one embodiment, this is performed by inserting a section of dialysis tubing into a flexible outer sleeve. The fractionation channel 34 then comprises the channel inside the dialysis tubing, and the region between the inner tubing and the outer sleeve comprises the precipitation reagent channel 48.

Another advantageous technique for accomplishing an easily centrifuged channel configuration is illustrated in FIG. 5. In this embodiment, the fractionation channel 34 is formed by cutting a spiral groove 84 into the surface of a plastic disk 86. The precipitation reagent channel 48 is formed by cutting a groove 88 into a second plastic disk 90. In one specific embodiment, the discs 86, 90 are made from polyethylene and are approximately 13.6 cm in diameter and 1.5 cm thick. In this embodiment, the grooves 84, 88 each may be approximately 1.5 mm wide, 2 mm deep, and have a total length of approximately 2 m. Each groove has a total volume of approximately 5 ml. The ends of the grooves 84, 88, are in fluid communication with fluid channels (not shown) within one or both discs 86, 90 to allow access to the inlet and outlet ends of both channels.

Figure 6:
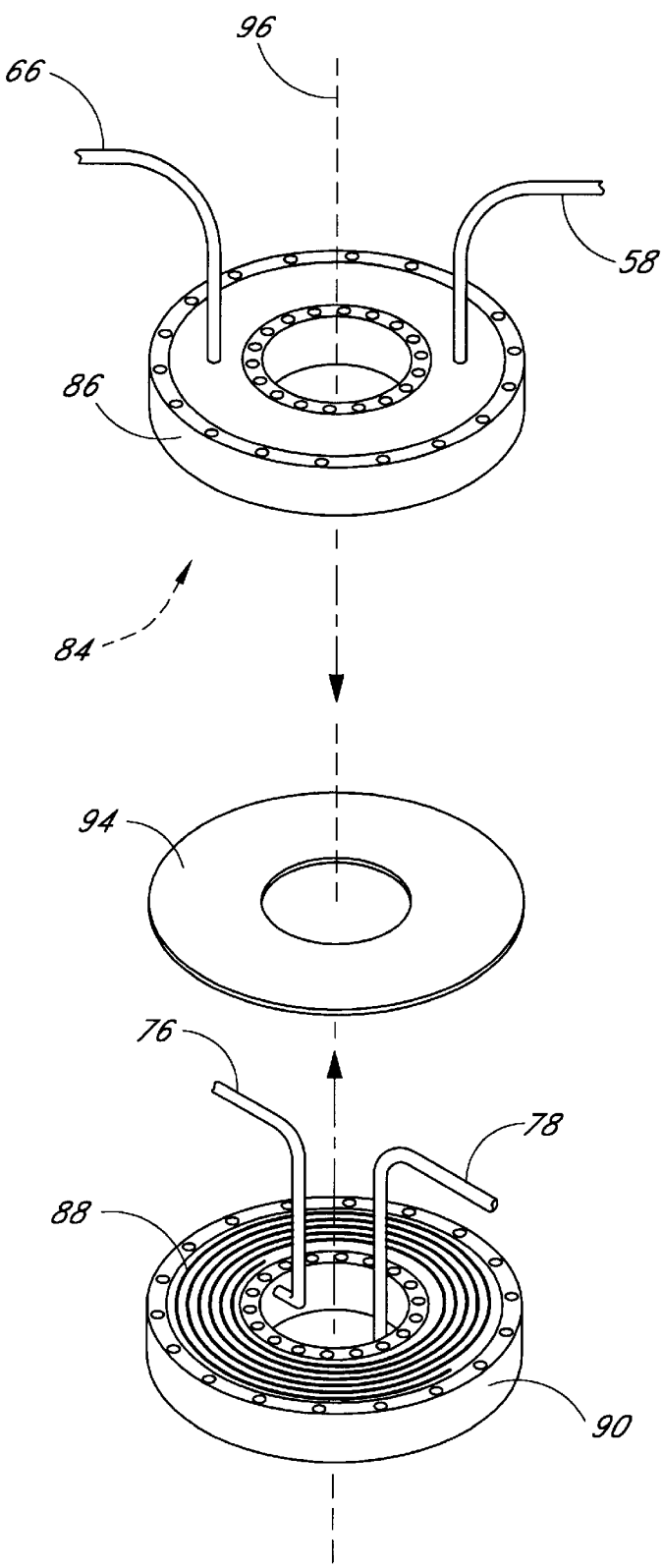
FIG. 6 is a perspective view of the disks of FIG. 5 sandwiching a semi-permeable membrane.

The two grooves 84, 88 may advantageously be formed as mirror images of one another so that when one disc 86 is placed on the other, the two grooves mate. As illustrated in FIG. 6, a semi-permeable membrane 94 may be sandwiched between the two discs 86, 90, and thus between the two mating grooves, thereby forming the dual channel configuration illustrated in FIG. 2. In one embodiment, the membrane is made from regenerated cellulose, and has a molecular weight cutoff of approximately 12,000 to 14,000 daltons. Each end of each groove 84, 88 is in fluid communication via an internal passageway to their respective connecting tubes 58, 66, 76, 78 shown in FIG. 4. These internal passageways may be directed out of the outer surface of the disk, as illustrated in upper disk 86 of FIG. 6. Alternatively, a slanted hole may be drilled such that the channel ends couple to holes on the inner cylindrical surface of the disk. This configuration is illustrated for the lower disk 90 of FIG. 6.

To produce the centrifugal field, the disc assembly of FIGS. 5 and 6 is rotated about its central axis 96 in a flow through centrifuge. In one advantageous embodiment, the flow through centrifuge apparatus is constructed without requiring the use of rotating seals. The principles behind these types of flow through centrifuges are described in detail in U.S. Pat. No. 3,856,669 to Ito, et al. and U.S. Pat. No. 4,425,112 to Ito. The disclosures of both of these references are hereby incorporated by reference in their entireties. One embodiment of such an apparatus is illustrated in FIG. 7.

Figure 7:
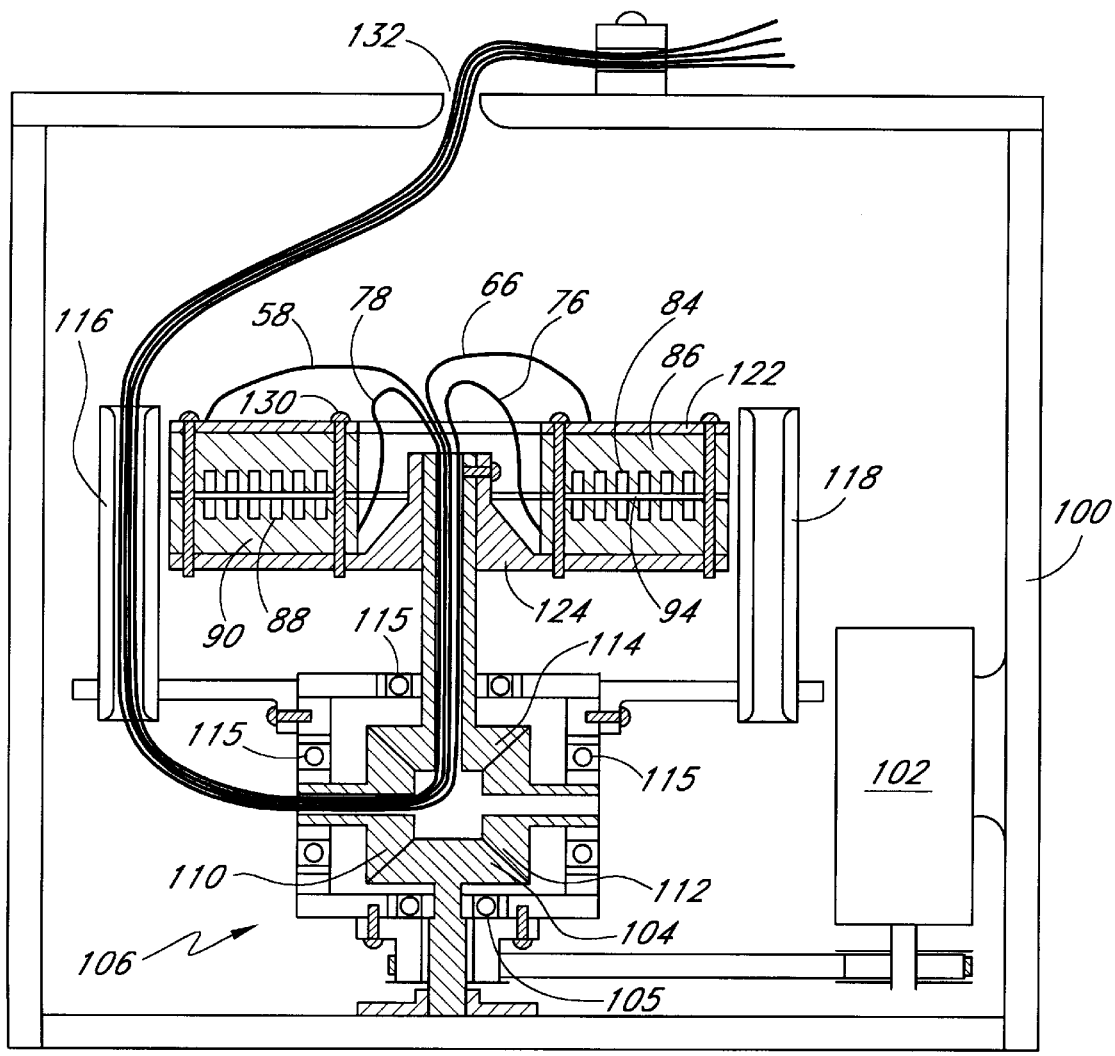
FIG. 7 is a partial cross section of a fractionation apparatus according to one advantageous embodiment of the invention.

In FIG. 7, a suitable flow through centrifuge is illustrated which comprises a housing 100 having a motor 102 and a miter gear 104 which is fixed to the housing 100 so as to be stationary relative to the housing 100. The motor 102 can be mounted to the side of the housing 100, and the stationary miter gear is advantageously fixed to the bottom of the housing 100. Mounted on the stationary miter gear 104 is a gear box 106, the housing of which is coupled to the stationary miter gear 104 with a bearing 105. The gear box 106 includes two horizontal miter gears 110, 112 in contact with the lower stationary miter gear 104. The gearbox also includes an upper vertical miter gear 114 in contact with the two horizontal miter gears 110, 112. Each of these other miter gears 110, 112, 114 are also coupled to the gear box housing via bearings 115.

The shaft of the motor 102 is coupled to the base of the gear box 106 by a drive belt 120. Thus, when the shaft of the motor 102 rotates at an angular velocity of $\omega$, the entire gear box rotates at velocity $\omega$ on the stationary miter gear 104. This causes the horizontal miter gears 110, 112 to rotate at a speed of $\omega$ within their gearbox bearings 115. The rotation of the horizontal miter gears 110, 112 causes upper vertical miter gear 114 to rotate at a speed of $\omega$ relative to the gearbox 106. Thus, because the entire gearbox 106 is already rotating relative to the housing 100 at a speed of $\omega$, the shaft of the upper miter gear rotates at a speed of $2\omega$ relative to the housing.

To perform the centifugation, the discs 86, 90 are pressed tightly together between an upper aluminum plate 122 and a lower aluminum plate 124 and held together with screws 130 placed around the inner and outer periphery of the grooved sections of the discs 86, 90, thereby forming a leak free seal between the grooves 84, 88 and the membrane 94. This assembly is then mounted on the upwardly extending shaft of the upper miter gear 114 so as to rotate at a speed of $2\omega$ relative to the housing 100. The four connecting tubes 58, 78, 66, 76, one for each end of each channel, are routed down through a hollow central portion of the shaft of the upper miter gear 114, and then out of the gearbox 106 through a hollow central portion of a horizontal miter gear 110. The connecting tubes then are routed up through one 116 of two arms 116, 118 and out an opening 132 in the top of the housing 100. In this embodiment no rotating seals are required, because the horizontal rotation of the tubes 58, 78, 66, 76 within the horizontal miter gear 110 cancels the other tube rotations relative to the housing 100 such that at the exit opening 132, no tube rotation is occurring. Centrifugation apparatus of this fundamental design is commercially available from Pharma-Tech Research Corporation of Baltimore Md. The elimination of rotating seals is especially advantageous in the present apparatus because cross flow and contamination at the connections between the inlet/outlet tubes and the spiral channels can be substantially avoided. The motor speed may of course vary widely depending on the diameter of the disk assembly and the desired application. For many applications, a motor speed of 500 to 700 RPM is suitable. In some advantageous embodiments, the motor speed is set at approximately 1000 RPM, thus resulting in a disc assembly 86, 90 rotation rate of 2000 RPM.

Preliminary experiments on the behavior of this fractionation apparatus determined that gravity plays an important role in ammonium sulfate transfer across the membrane 94. When the fractionation channel is the upper channel 84, the ammonium sulfate which migrates through the membrane 94 to the upper channel 84 remains over the membrane 94, thereby reducing the transfer efficiency. In contrast, when the fractionation channel is the lower channel 88, ammonium sulfate moves to the bottom of the fractionation channel after passing through the membrane 94 such that the less dense water solvent is exposed to the membrane surface and transfer efficiency is increased. Applying a centrifugal force field appears to enhance this affect, as ammonium sulfate in the fractionation channel is forced to the distal wall of the lower channel 84, thereby allowing increased net migration of ammonium sulfate across the remainder of the membrane.

It was also found that the greater the rate of solvent flow in the fractionation channel relative to the flow in the precipitation reagent channel, the lower the concentration of precipitation reagent in the eluate from the fractionation channel. If, for example, a 1 ml/min flow rate of 95% saturated ammonium sulfate is present in the precipitation channel and a 1 ml/min flow rate of water is present in the fractionation channel, the eluate from the fractionation channel is approximately 10% saturated with ammonium sulfate. In contrast, with a 0.1 ml/min flow rate of water in the fractionation channel, the eluate from the fractionation channel is near 90% saturated with ammonium sulfate.

Another phenomenon that has been noted to occur is that the output flow rate of the fractionation channel decreases as a percentage of the input flow rate as the input flow rate is decreased. This is due to solvent migration from the fractionation channel to the precipitation reagent channel, where it exits from the outlet of the precipitation reagent channel. At a 0.1 ml/min fractionation channel flow rate at the inlet, less than 0.25 ml/min is captured at the fractionation channel outlet. As will be described further below, however, no significant amount of target species appears to be lost to the precipitation reagent channel. Thus, this phenomenon helps to further concentrate the target species in the solvent eluate.

Turning now to FIGS. 8 through 14, several examples of species separation and purification using the principles of the invention are set forth.

EXAMPLE 1

Separation of Albumin and Gamma Globulin

In the apparatus of FIG. 7, the lower channel was initially filled with a 95% saturated solution of ammonium sulfate, and a 1 ml/min flow of 95% saturated solution of ammonium sulfate was introduced into the upper channel with a Shimadzu gradient pump. A sample of 4 mg each of albumin and gamma globulin (Sigma Chemical Co.) in 1 ml of 50 mM potassium phosphate (pH 6.8) was introduced into the lower channel, and a 0.06 ml/min flow of 50 mM potassium phosphate (pH 6.8) was initiated through the lower channel with a Harvard Apparatus syringe pump. The disks were centrifuged at 2000 RPM (1000 RPM at the motor). The 275 nm absorbance of the eluate was monitored with an LKB Uvicord S. An LKB Ultrorac collected 20 min. duration fractions of the eluate. The ammonium sulfate concentration in the upper channel was held at 95% saturation for four hours, and was then linearly dropped to 0% over the following 22.5 hours.

Figure 8:
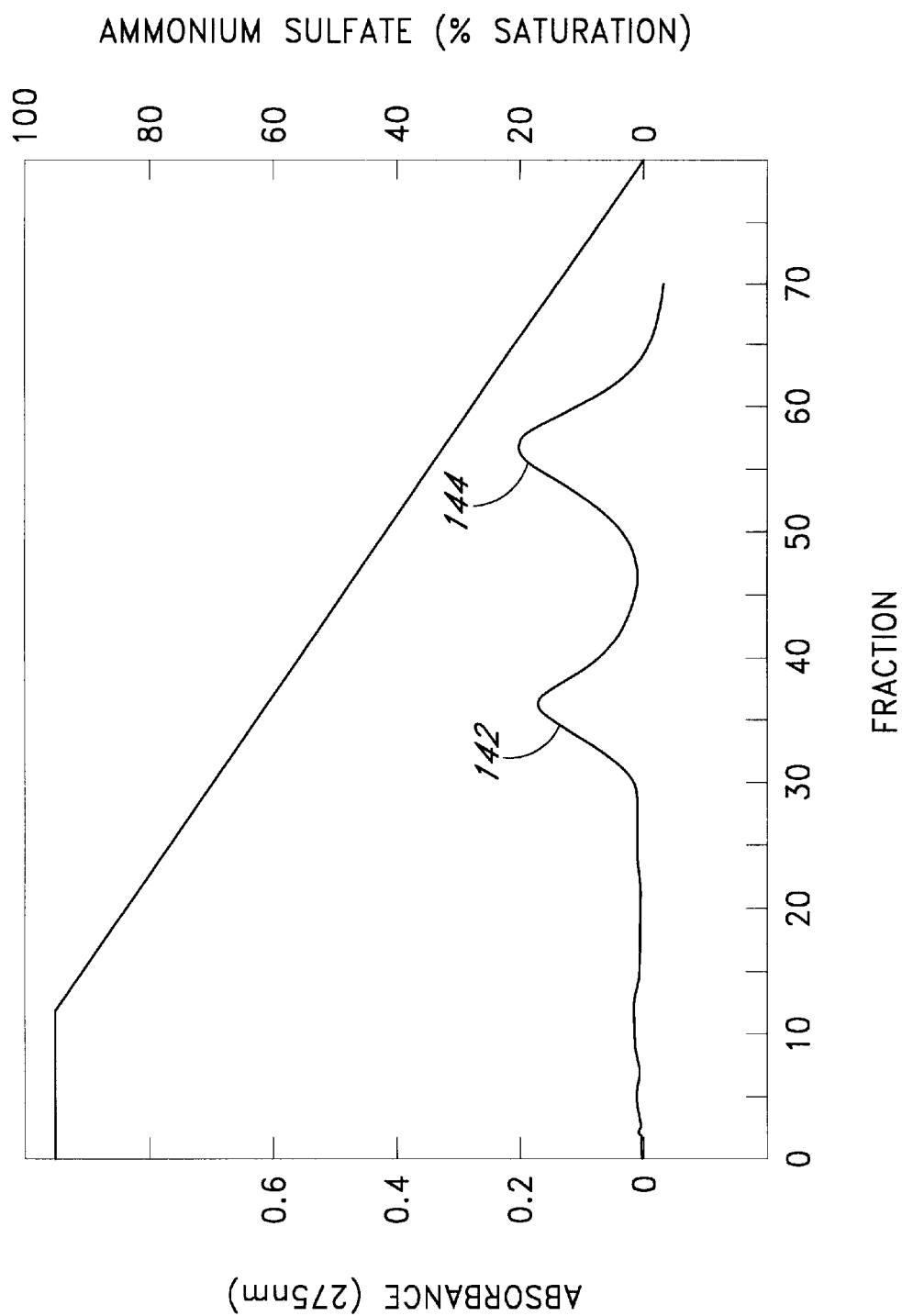
FIG. 8 is a graph illustrating the UV-absorbance of eluate as a function of time for a sample containing albumin and gamma globulin.
Figure 9:
FIG. 9 is a graph illustrating the UV-absorbance of eluate as a function of time for a sample of normal human serum.

FIG. 8 is a reproduction of a strip chart recording of the 275 nm absorbance of the eluate as a function of time. The albumin eluted first in peak 142 of FIG. 8 at about 60% ammonium sulfate saturation in the upper channel. The globulins were well resolved from the albumin, eluting in a second peak 144 at about 30% ammonium sulfate saturation in the upper channel approximately 6–7 hours later.

EXAMPLE 2

Separation of Normal Human Serum

Using the same conditions as Example 1, a sample of 100 μl of pooled normal human serum in 1 ml of 50 mM potassium phosphate was introduced into the lower channel. A graph of absorbance as a function of time for this experiment is presented in FIG. 9. Once again, the albumin peak 148 is well resolved from the globulin peak 150.

EXAMPLE 3

Separation of Monoclonal Antibody

The conditions for this purification protocol are the same as set forth in Example 1 above, except the starting concentration of ammonium sulfate in the upper channel was 75% saturated rather than 95% saturated, and a Perkin Elmer pump, rather than a Shimadzu pump, was used.

A 50 ml sample of hybridoma culture medium was obtained from Dr. Tadashi Okada, Department of Physiology, Aichi Medical University, Nagoya, Japan. The proteins in the crude supernatant were first concentrated by adding ammonium sulfate to 70% saturation to precipitate the target proteins. The sample was centrifuged, the supernatant was decanted, and the precipitate was redissolved in 2 ml of 50 mM potassium phosphate (pH 6.8). This 2 ml sample was introduced into the lower channel.

Figure 10:
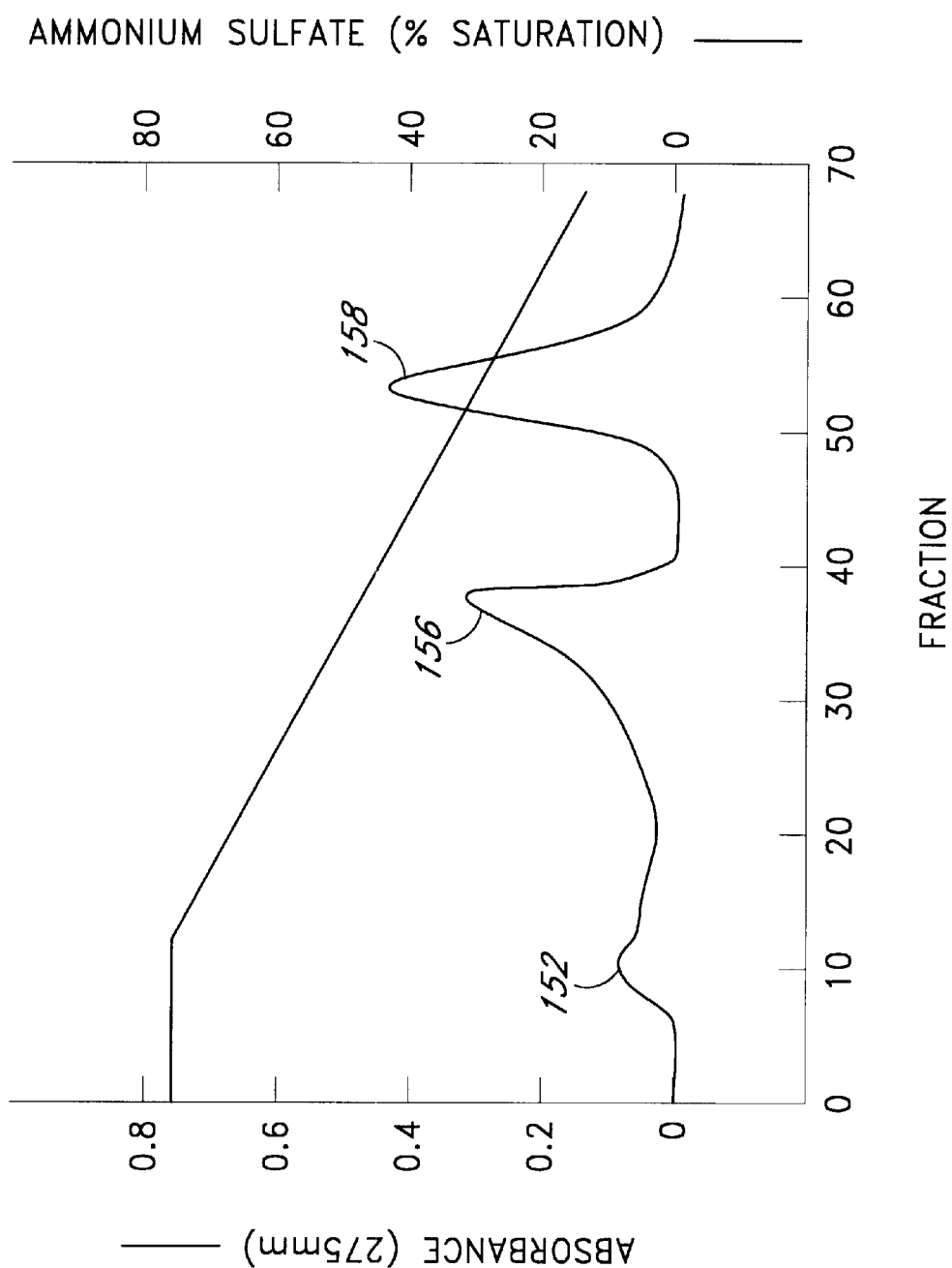
FIG. 10 is a graph illustrating the UV-absorbance of eluate as a function of time for a sample of hybridoma culture medium containing a monoclonal antibody.
Figure 11:
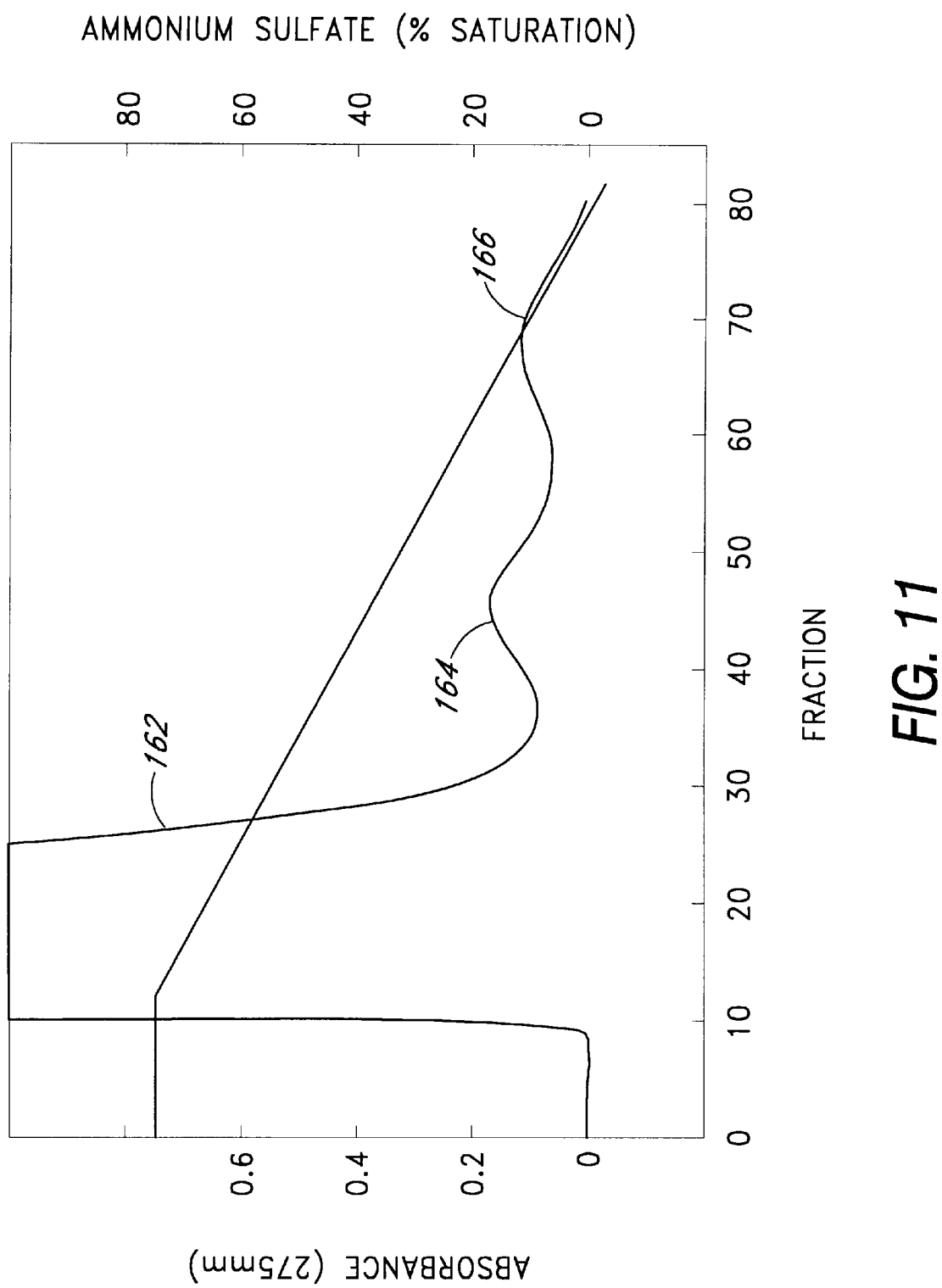
FIG. 11 is a graph illustrating the UV-absorbance of eluate as a function of time for a sample of rabbit reticulocyte lysate.

The absorbance at 275 nm as a function of time for this experiment is shown in FIG. 10. Albumin eluted in an initial peak 152. The antibodies were eluted in two peaks, an IgM peak 156, and an IgG peak 158. Activity testing with fractions collected in the IgM peak showed strong antibody activity of approximately 100 times that measured for the original crude sample.

EXAMPLE 4

Purification of Rabbit Reticulocyte Lysate

Studies of reticulocyte proteins require the initial removal of hemoglobin, which typically represents over 99% of the proteins present in a raw reticulocyte lysate. Under experimental conditions as described in Example 3, a 1 ml sample of crude rabbit reticulocyte lysate was introduced into the lower channel. The 275 nm absorbance was measured as a function of time, with the results illustrated in FIG. 11. The hemoglobin is eluted in a first peak 162 at about 60% ammonium sulfate saturation on the upper channel. The remaining proteins are eluted in two smaller peaks 164, 166 at a lower ammonium sulfate concentration. A comparison of UV absorbance measurements at 260 nm and 280 nm of the fractions collected during the peak 166 indicated that RNA was eluted with protein at this time.

EXAMPLE 5

Separation of Protein from Protein-PEG Conjugates

Figure 12:
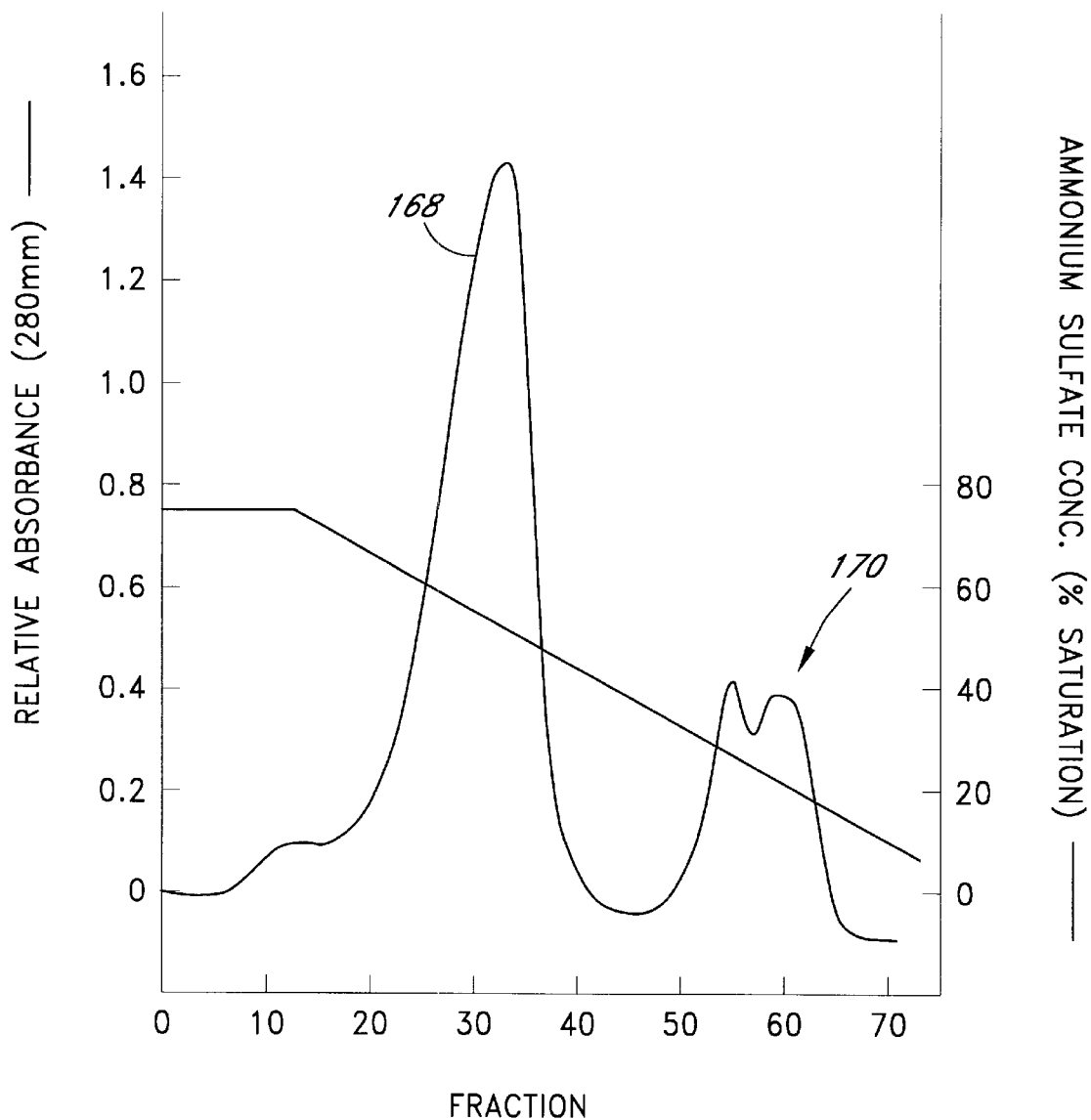
FIG. 12 is a graph illustrating the UV-absorbance of eluate as a function of time for a sample containing protein and protein-polyethylene glycol complexes.

Using the protocol of Example 3, 10 mg of a mixture of lysozyme and lysozyme conjugated to polyethylene glycol (PEG5000) molecules was introduced into the lower channel. 275 nm absorbance data for this experiment is provided in FIG. 12. The lysozyme elutes in a first peak 168, while the conjugated lysozyme molecules elute in a second peak 170. Within the second peak 170, lysozyme molecules conjugated to different numbers of PEG5000 molecules are partially resolved.

EXAMPLE 6

Isolation of Recombinant Ketosteroid Isomerase

Figure 13:
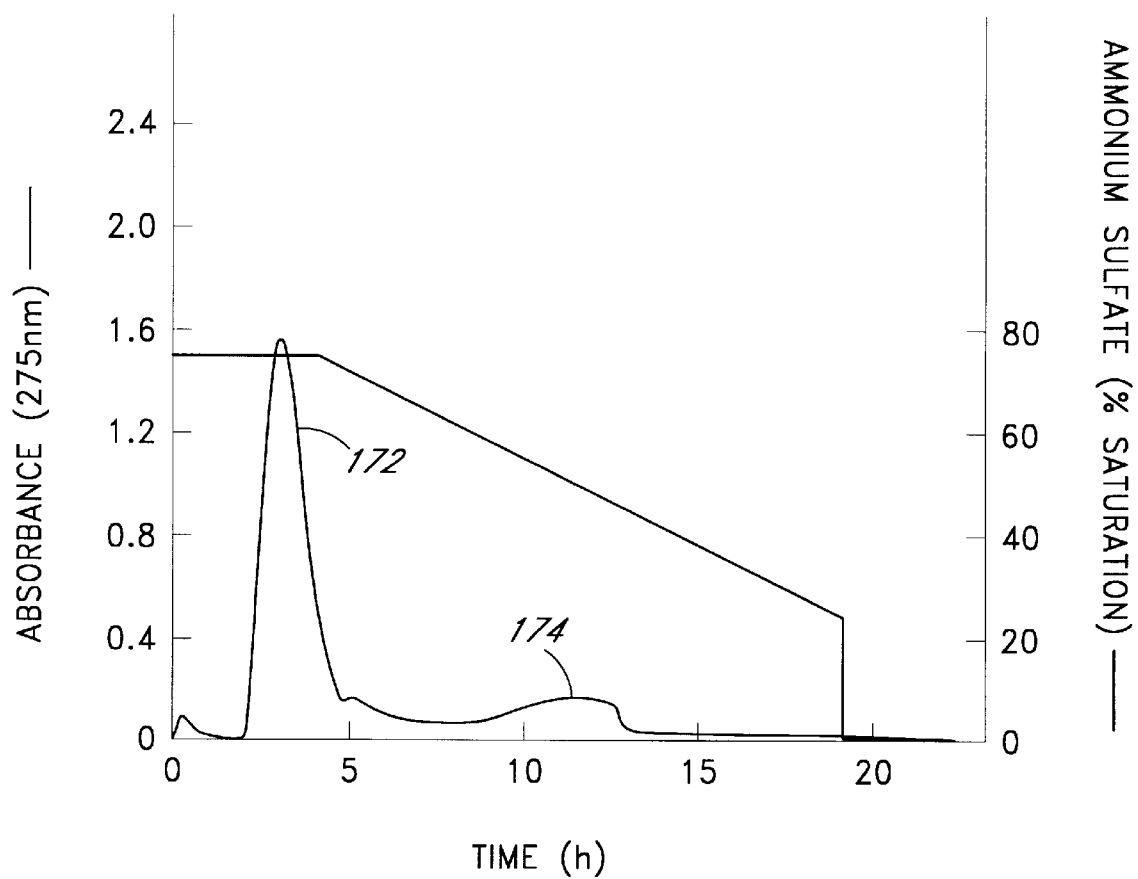
FIG. 13 is a graph illustrating the UV-absorbance of eluate as a function of time for a sample of E. coli lysate containing recombinant ketosteroid isomerase.

The separation protocol for recombinant ketosteroid isomerase (rKSI) from a crude *E. coli* lysate was performed under the conditions of Example 3, except the ammonium sulfate concentration in the upper channel was linearly dropped from 75% saturation to 25% saturation over 15 hours, at which time it was dropped straight to zero. The sample introduced was 0.5 ml *E. coli* lysate, containing approximately 1 mg rKSI protein. The results of this experiment are illustrated in FIG. 13. After elution of an unknown species or collection of species in an initial large peak 172, the rKSI eluted in a later peak 174 at approximately 50% saturated ammonium sulfate in the upper channel. However, the second peak 174 also contained many contaminating protein species other than the desired rKSI.

Figure 14:
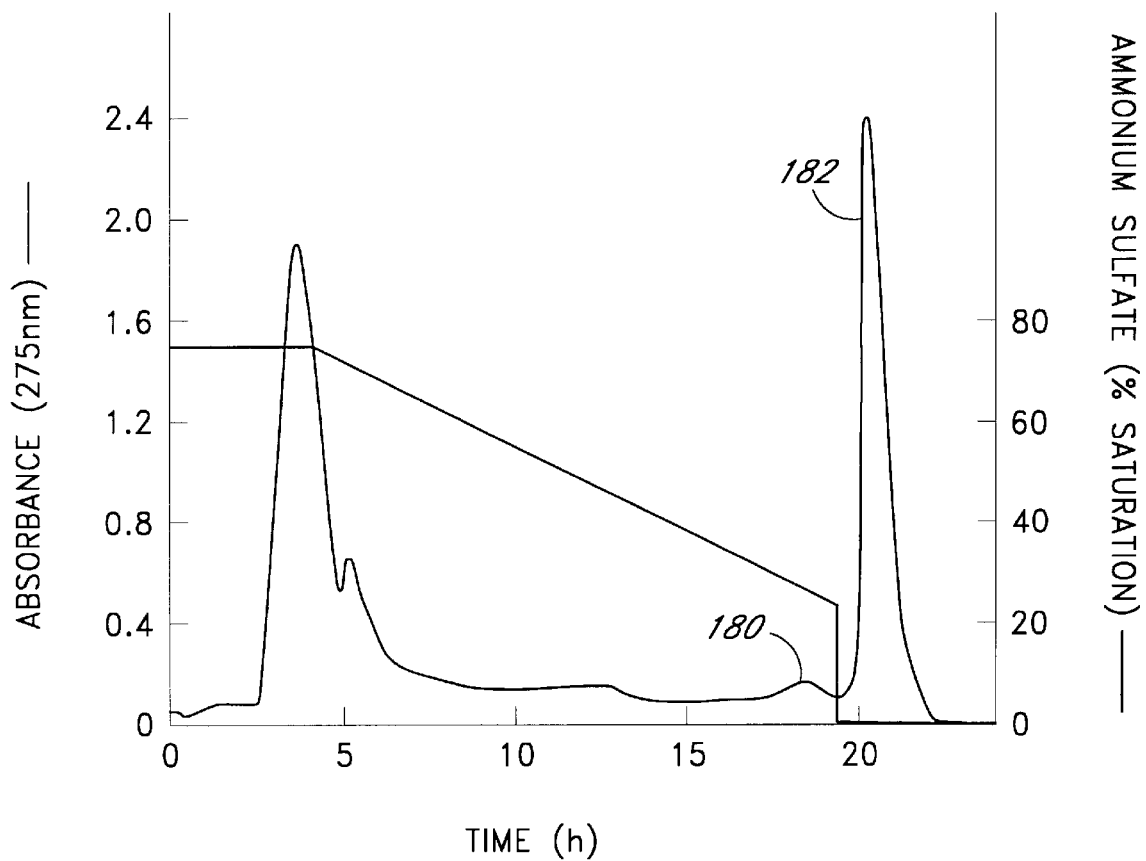
FIG. 14 is a graph illustrating the UV-absorbance of eluate as a function of time for a sample of E. coli lysate containing recombinant ketosteroid isomerase bound to an estradiol-polyethylene glycol ligand.

To improve the separation, approximately 25 mg of a specific affinity ligand β-estradiol-17-methyl-PEG-5000 was added to the sample. The results of the same separation protocol with the affinity ligand added to the sample shows a significant change in the elution pattern, which is illustrated in FIG. 14. With the added ligand, a small peak 180 elutes at a much later stage containing the protein-ligand complex. This peak is followed by a large peak 182 when free ligand exits the lower channel. SDS PAGE analysis of the collected fractions in both experiments showed a much lower concentration of contaminating proteins in the small peak 180 in the second experiment than in the rKSI containing peak 174 in the first experiment.

EXAMPLE 7

Separation of Small Molecular Weight Compounds

To test the tendency of sample species to migrate from the lower fractionation channel to the upper precipitation reagent channel, a membrane having a molecular weight cutoff of 6000–8000 daltons was used in the apparatus of FIG. 7, and a sample of the low molecular weight peptide bacitracin was introduced into the lower channel. Even though the bacitracin has a lower molecular weight than the cutoff of the membrane, no bacitracin was observed to migrate across the membrane and elute from the upper channel. This result suggests that as long as a target species is not soluble in the solution of precipitation reagent, the dialysis membrane is not required to maintain the target species in the fractionation channel. Thus, low molecular weight species may be separated with large pore dialysis membranes separating the two channels.

This finding opens up a rich domain of applications to the separation and purification of small molecules. For example, two mutually miscible organic solvents such as ether or hexane and ethanol can be used for fractional precipitation of analytes according to their differences in solubility in the different solvents, provided they are much more soluble in one solvent and than in the other.

The fundamental fractionation principles presented above and applied to protein separation may also be applied to cell separation. In this application, a polymeric precipitation reagent is used to create a density gradient from one end of a fractionation channel to other. Populations of different cell types introduced into this channel are sedimented in different locations along its length, and are accordingly eluted in order of increasing specific gravity when the solvent density along the entire channel is slowly increased.

Figure 15:
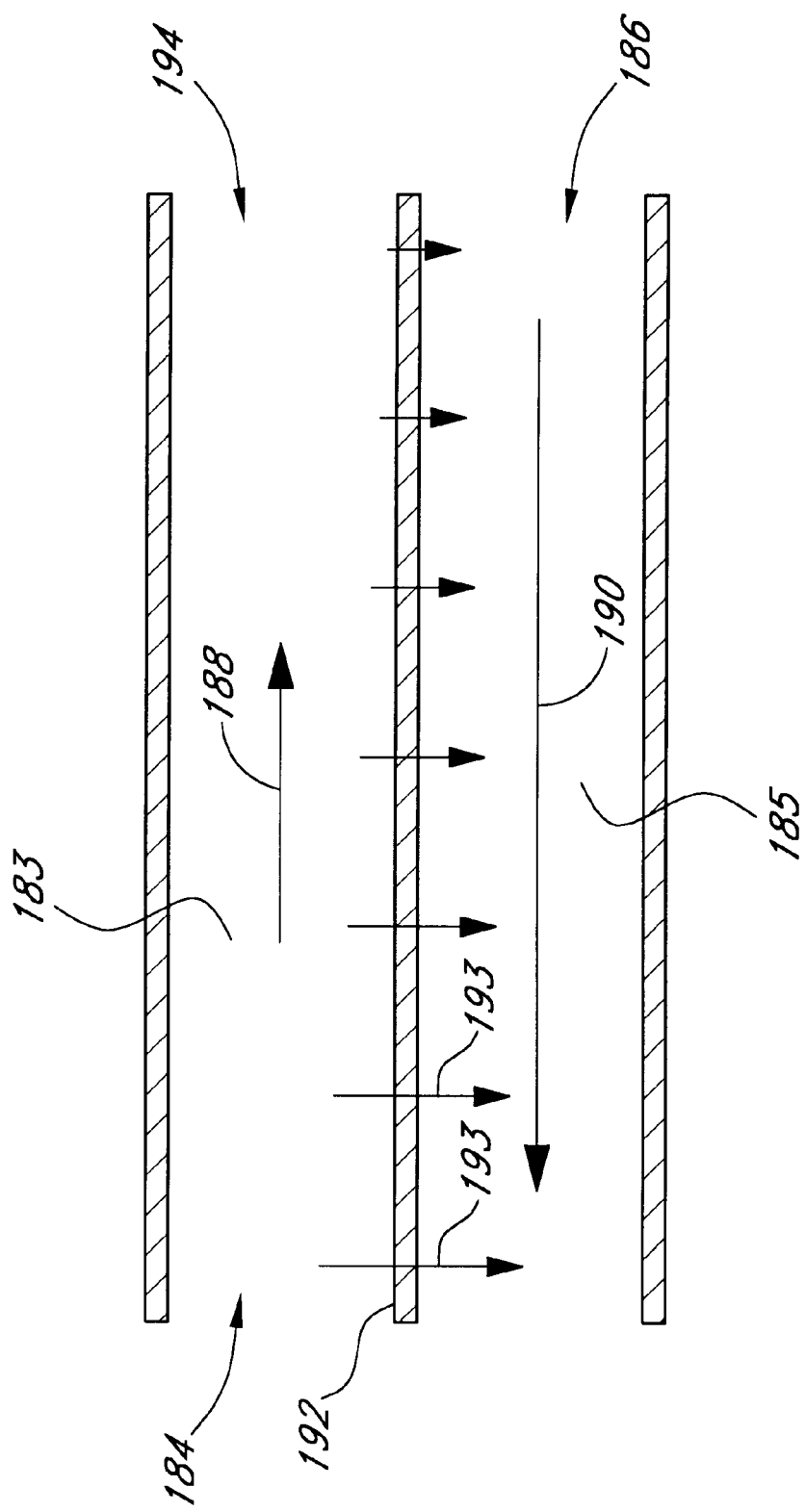
FIG. 15 is a cross section of another embodiment of a dual channel fractionation apparatus that may be used to produce a position dependent concentration of precipitation reagent in the channel of FIG. 1.

FIG. 15 illustrates a dual channel fractionation apparatus configured for cell separation in accordance with this technique. The apparatus is structurally similar to the apparatus illustrated in FIG. 2. In this embodiment, however, the upper channel 183 receives from an inlet port 184 an isotonic inert polymer solution having a high density relative to pure water. Advantageously, the density of the polymer solution is greater than approximately 1.1. The lower channel 185 receives a potassium phosphate buffered saline solution from its inlet port 186. The two inlet ports 184, 186 are located on opposite ends of the channel pair, such that the polymer solution flows from left to right in the direction of arrow 188, and the saline solution flows from right to left in the direction of arrow 190. Initially, the saline solution flow rate in the lower channel 185 is set to be much greater than the flow rate of polymer solution in the upper channel 183.

As with the apparatus illustrated in FIG. 2, the two channels 183, 185 are separated with a semi-permeable membrane 192. However, for cell separation applications the pore size of the membrane should be very large so that high molecular weight polymer molecules can pass through from the upper channel 183 to the lower channel 185. For example, commercially available microfilters having a pore size of 0.25 to 0.8 micrometers are suitable for allowing the polymer to migrate into the lower channel while retaining sample cells to be separated in the upper channel. As illustrated by arrows 193, net migration of polymer will be highest where the polymer concentration is highest in the upper channel, which will be in the region near the inlet 184 of the upper channel 183. Net migration decreases near the inlet 186 of the lower channel 185 because the polymer concentration in the upper channel 183 steadily decreases from the inlet 184 to the outlet 194. If the flow rate of buffer solution in the lower channel 185 is much greater than the flow rate of polymer solution in the upper channel 183, the concentration of the polymer will decrease approximately exponentially from the inlet 184 to the outlet 194. This is illustrated in FIG. 16A.

Figure 16:
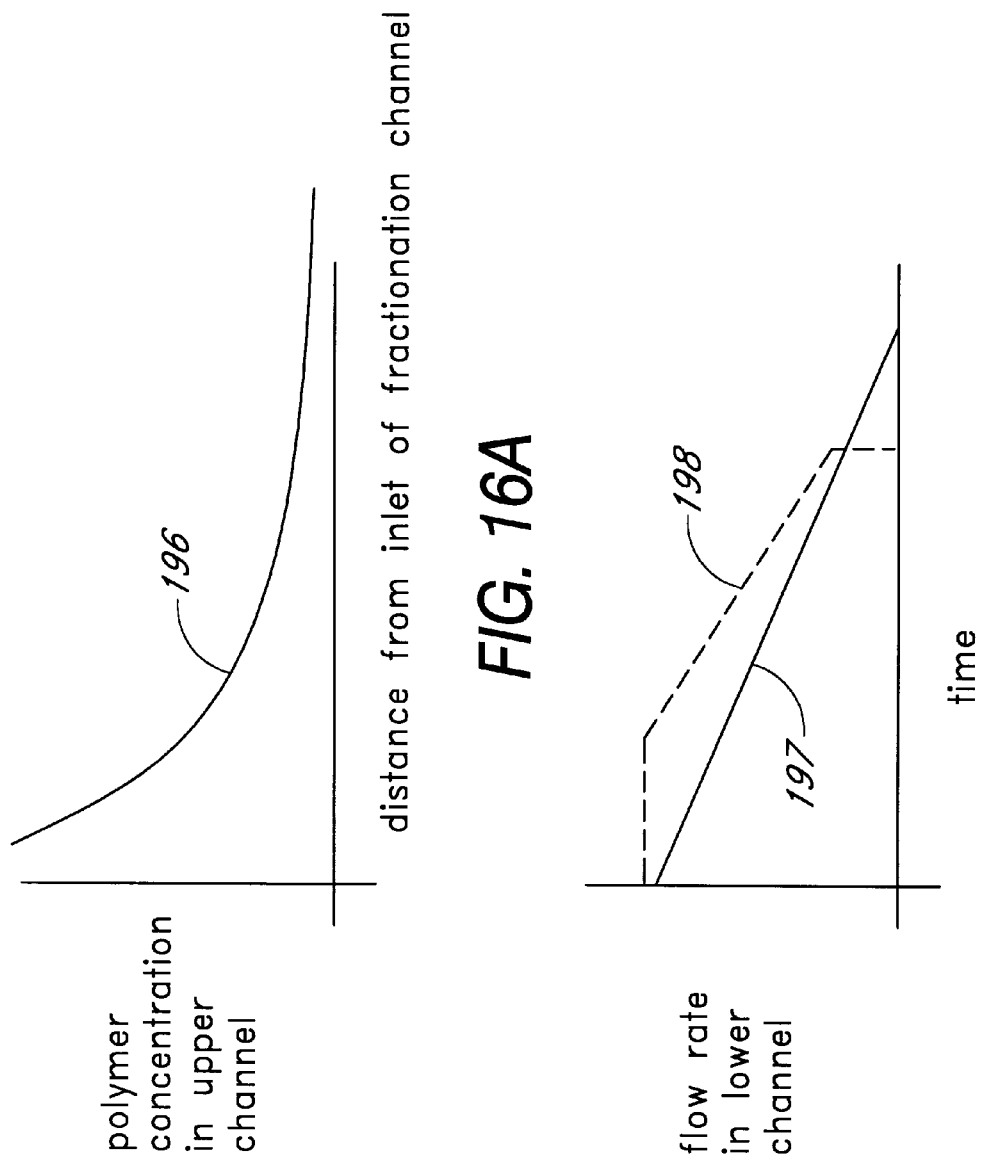
FIG. 16A is a graphical representation of the concentration of precipitation reagent as a function of position that is advantageously produced in the upper sample channel of FIG. 15.
FIG. 16B is a graphical representation of the concentration of the flow rate as a function of time in the lower channel of FIG. 15.

Referring now to FIG. 16A, a graph of the approximate functional dependence of the polymer concentration on channel position is shown. The curve 196 approximates the exponential form $Ce^{-kx}$, wherein C and k are constants, and wherein x is the distance from the inlet end 184 of the channel. The constants C and k will be dependent on the initial concentration of polymer at the inlet and the characteristics of the membrane 192, among other things. The channel pair 183, 185 may be advantageously formed as spiral grooves in a mated pair of disks as described above, and utilized in the seal free centrifuge illustrated in FIG. 7. Typically, the channels will be shorter in length and larger in cross section than the channels used for protein fractionation. A cross section of 0.5 cm×0.5 cm and a length of approximately 1–2 meters is suitable in many applications, although the dimensions of the optimum channel will vary with cell type and desired sample size.

A cell separation protocol is initiated by flushing both upper channel 183 and the lower channel 185 with the phosphate buffer solution while rotating the channels in a centrifuge as shown in FIG. 7. A cell suspension is then introduced into the upper channel inlet 184. After the cells are sedimented near the inlet, a high density polymer solution is introduced into the inlet 184 of the upper channel 183.

As the lower channel 185 is being flushed at a relatively high rate with the saline solution, the exponentially decreasing polymer concentration, and thus density profile, is created in the upper channel 183 as illustrated in FIG. 16A. The cells in the channel are thus exposed to the density gradient, and the lower specific gravity cells migrate toward the outlet end 194 of the upper channel 183 until they are re-deposited at a point farther down the channel 183.

As illustrated in FIG. 16B, the flow rate of saline in the lower channel is then decreased over time. This decrease may be continuous, as shown by the linear curve 197, or may be discontinuous as shown by the curve 198 of FIG. 16B. In either case, the reduction of flow rate in the lower channel 185 results in a timewise increase in the polymer concentration all along the length of the upper channel 183. Consequently, and in analogy with the protein separation protocols described above, the sedimented cells will move down the channel until reaching another critical density point, where they will be re-deposited. The cells finally elute from the outlet 194 of the upper channel 183 in the order of increasing specific gravity.

It is possible to perform a related cell separation protocol using a single channel. In this embodiment, a gradient pump has a high density polymer solution as one input and water or saline solution as a second input. The output of the gradient pump is coupled to the input of the sample channel 183. In this embodiment, a steadily increasing concentration of polymer is fed to the inlet 184 of the channel 183. In this method, sedimented cells will float out of the channel at the point where the density of the polymer solution rises to the critical density for the given cell type.

The dual channel embodiment has several advantages, however. First, in the dual channel design of FIG. 15, the point of critical density for a given cell type may move toward the outlet end of the channel at a lower rate than the fluid flow rate. Thus, cells are subject to repeated sedimentation, enhancing separation. In the single channel embodiment, once the cells are floated by the critical density solvent solution, they move down the channel with the gradient, and are not re-sedimented. They are thus subject to band broadening during this elution period as they travel toward the outlet of the channel.

Figure 17:
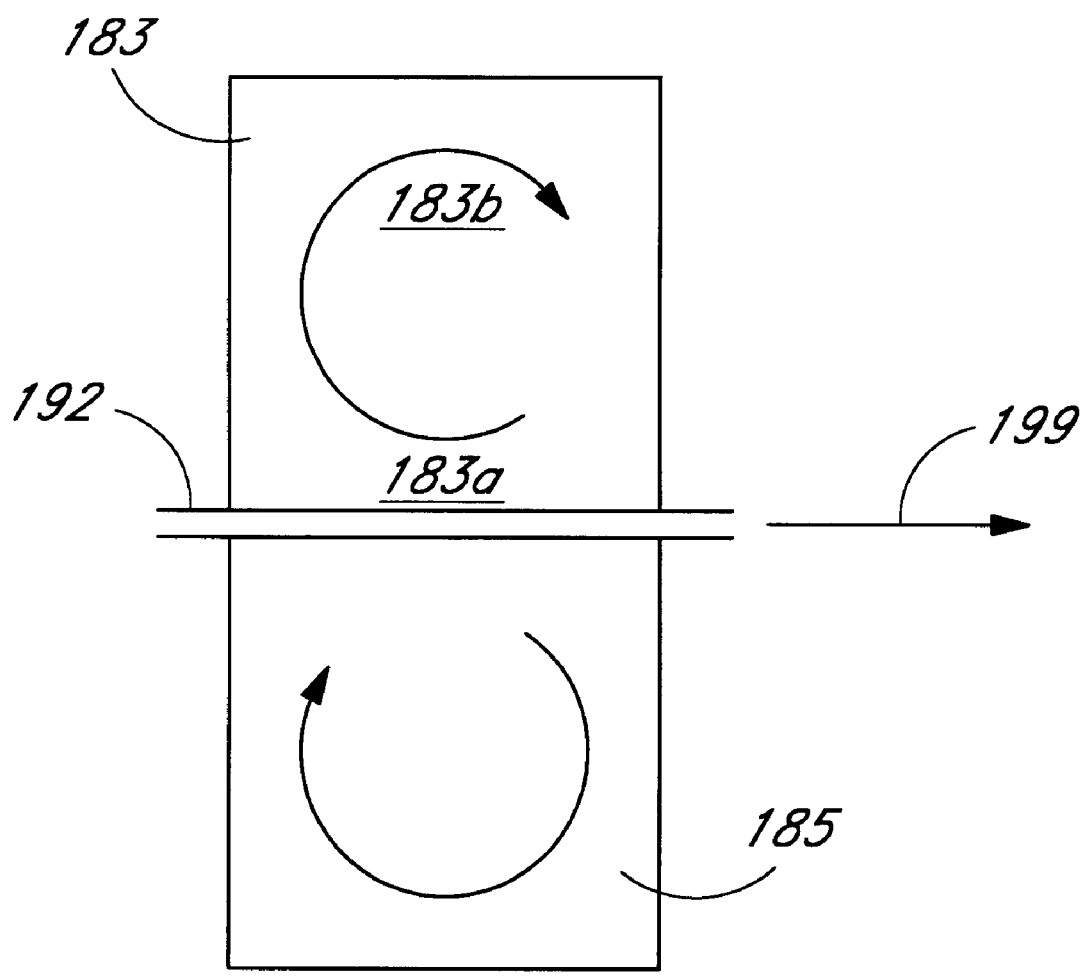
FIG. 17 is a transverse cross section of the dual channel apparatus of FIG. 15.

In addition, because of the exchange of water and polymer through the membrane, a circular flow in a plane transverse to the channel's longitudinal axis is generated at every point along the fractionation channel. This is illustrated in FIG. 17. Because of water migration up through the membrane 192, and polymer migration down through the membrane 192, the density of the solvent in the upper channel 183 is lower at the channel bottom 183a than it is at the channel top 183b. The higher density material at the upper region 183b is forced more strongly in the direction of the centrifugal force field (indicated by arrow 199) than is the lower density material near the membrane 192. Thus, flow toward the distal wall in the upper region 183a and flow away from the distal wall in the lower region is produced, resulting in a circular mixing effect in the channel 183. This mixing gently disperses the sedimented cells to help prevent packing and cell aggregation that interferes with effective fractionation.

Returning now to the molecular (rather than cellular) fractionation techniques, it will be appreciated that effective use of the fractionation apparatus and methods described above may be improved if it were possible to predict with some accuracy the retention times and peak widths of common protein species which need to be isolated from one another or from an unknown target molecule. Accurate data regarding such precipitation points is difficult to find in the literature, and may be somewhat different under the continuously variable precipitation reagent concentration conditions present in the fractionation channel.

Figure 18:
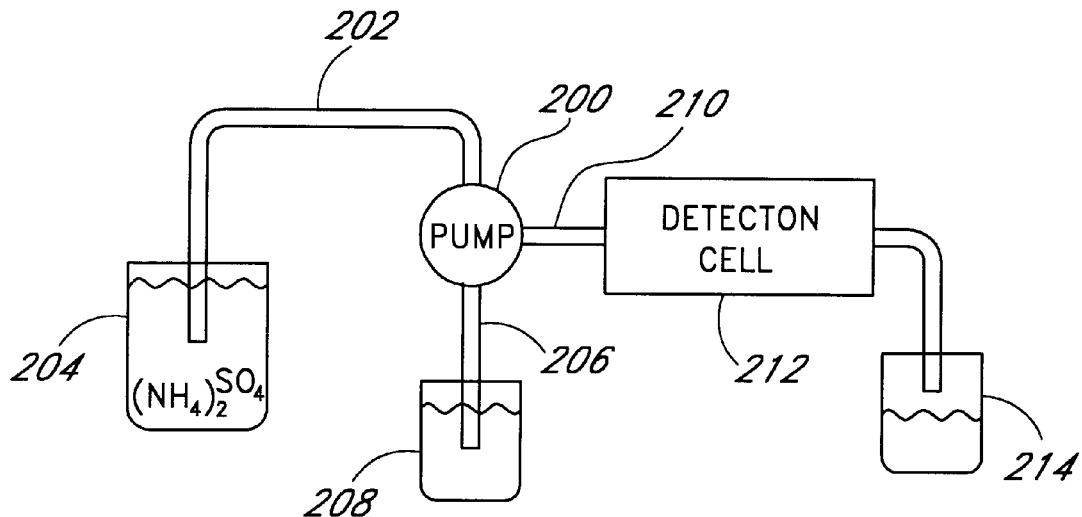
FIG. 18 is an overall block diagram of another sample precipitation apparatus.

To obtain useful data on this subject, a precipitation point analysis apparatus may be constructed as shown in FIG. 18. Referring now to this Figure, a gradient pump 200 has one inlet 202 coupled to a reservoir 204 of a high concentration of precipitation reagent, such as 90% saturated solution of ammonium sulfate. The second inlet 206 of the gradient pump 200 is coupled to a reservoir of protein solution for which information regarding precipitation properties is desired. The outlet 210 of the gradient pump 200, which has an output comprising a varying contribution from the first 202 and the second 206 inlets, feeds a detection cell 212, following which the detection cell 212 output is collected in a waste container 214.

Figure 19:
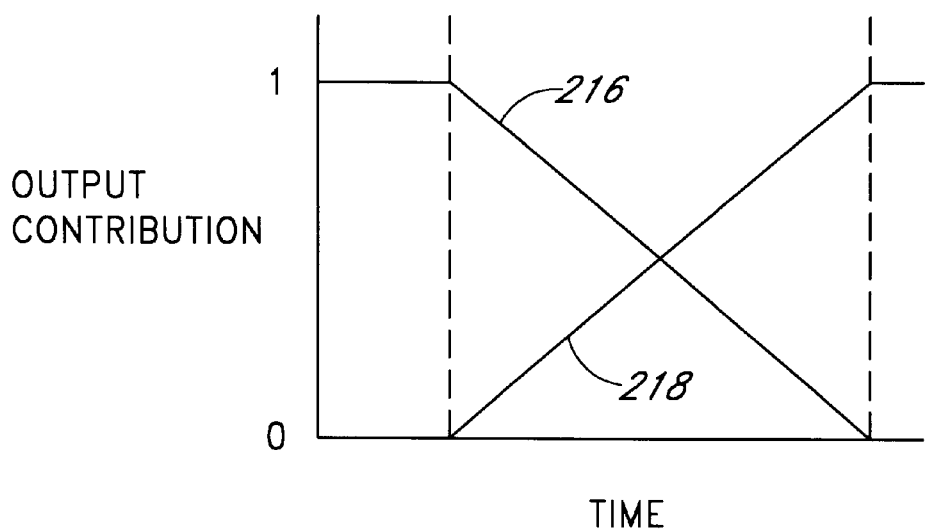
FIG. 19 is a graph illustrating the relative contributions of sample and precipitation reagent output by the gradient pump of FIG. 15 as a function of time.

With this apparatus, the contribution to the pump output from the source of precipitation reagent 204 may be increased over time, and the contribution to the pump output from the source of sample material 208 may be decreased over time. One embodiment of this pump 200 programming is illustrated in FIG. 19. In this Figure, the contribution to the output of the gradient pump which comes from the sample reservoir 208 is shown by curve 216 which begins at 1 or 100%. The contribution to the output of the gradient pump which comes from the precipitation reagent reservoir 204 is shown by curve 218 which begins at 0 or 0%. After a few minutes of 100% sample, the contribution from the precipitation reagent reservoir 204 is ramped up, partially replacing the sample solution, until the output of the gradient pump 200 is 100% precipitation reagent solution and no sample.

In operation, the UV absorbance of the eluate will initially fall as the concentration of protein in the output of the pump 200 drops. However, when the precipitation reagent concentration rises sufficiently, and the protein in the output begins to form a precipitate, light scattering will cause the absorbance reading to increase. Once all the protein in the eluate is precipitated completely, the absorbance reading will decrease again as the total concentration of protein in the eluate continues to fall to zero at the endpoint of the procedure. If desired, the detection cell may be flushed of precipitation reagent by recoupling the sample reservoir 208 to the pump output 210 for a few minutes following the conclusion of the procedure. This is illustrated in Example 8.

EXAMPLE 8

Continuous Ammonium Sulfate Precipitation of Human Albumin 5 mg/ml human albumin was dissolved in plain water. A reservoir of this protein solution was coupled to one inlet of a Perkin-Elmer Series 200 gradient pump. The other inlet of the gradient pump was coupled to a reservoir of 90% saturated ammonium sulfate. The gradient pump total output was set to 0.1 ml per minute, and was programmed to draw output flow 100% from the protein reservoir for 3 minutes. Over the following 60 minutes, the output contribution from the protein reservoir was linearly ramped to zero, while the contribution from the ammonium sulfate reservoir was linearly ramped to 100%. For the following 5 minute period, the pump was programmed to again draw 100% from the protein reservoir.

Figure 20:
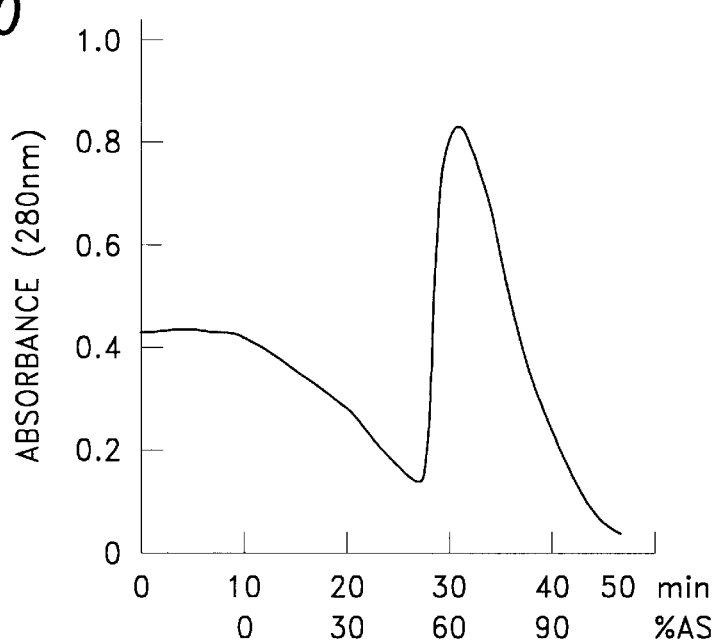
FIG. 20 is a graph illustrating the UV absorbance of eluate from the apparatus of FIG. 18 as a function of time for a sample of human albumin.

The output of the gradient pump was continuously monitored at 280 nm by a Uvicord S absorbance monitor, the output of which is shown in FIG. 20. As described in general above, the absorbance of the eluate decreases until 27 minutes into the procedure, at an ammonium sulfate concentration of 56%. The elution curve reaches a maximum absorbance at 32 minutes, at an ammonium sulfate concentration of 68% saturated. The precipitation point for human albumin under the conditions of a continuously increasing ammonium sulfate gradient is thus determined to be approximately 62%.

The above technique was performed on a wide variety of protein species. Most of these proteins precipitate completely in a relatively narrow range of 10–12% difference in ammonium sulfate saturation of the output solution. Human albumin, illustrated in Example 8, is one such protein. Other proteins such as alpha-globulin and myoglobin showed broader or indistinct peaks which suggest sample heterogeneity. Cytochrome-c from horse heart showed no evidence of precipitation even at 90% ammonium sulfate saturation. Trypsinogen from bovine pancreas precipitated almost immediately at an ammonium sulfate concentration of less than 5% saturated. The effect on precipitation point due to changes in protein concentration has also been evaluated. For Isozyme, for example, it has been found that the precipitation point is stable at about 50–53% ammonium sulfate saturation in the concentration range of 2.5 to 10 mg/ml. As the protein concentration decreases below this level, however, the precipitation point increases to about 75% ammonium sulfate saturation at 0.1 mg/ml. It has also been found that the precipitation points of several proteins are pH dependent. This is illustrated in Example 9.

EXAMPLE 9 pH Dependence of Ammonium Sulfate Precipitation Points 5 mg/ml solutions of the following proteins were subjected to the procedure of Example 8 at pH 4.5, 6.7, and 9.0: cytochrome-c, human albumin, ovalbumin, bovine hemoglobin, lysozyme, α-chymotrypsin, human α-globulin IV-1, human α-globulin IV-4, human β-globulin, human γ-globulin, bovine γ-globulin, and fibrinogen. The results are set forth in FIG. 21.

These proteins may be divided into two major groups. The hemoglobin and albumin which have a high precipitation point at approximately the 60–65% range, and the globulins and fibrinogen which have a relatively low precipitation point of approximately the 35–45% range. Proteins of the first group tend to have increasing precipitation points with increasing pH, whereas proteins of the second group generally show an opposite trend of decreasing precipitation points at high pH. This indicates that fractionation efficiency for samples containing mixtures of these types of proteins may be improved by performing the procedure at high pH.

Figure 21:
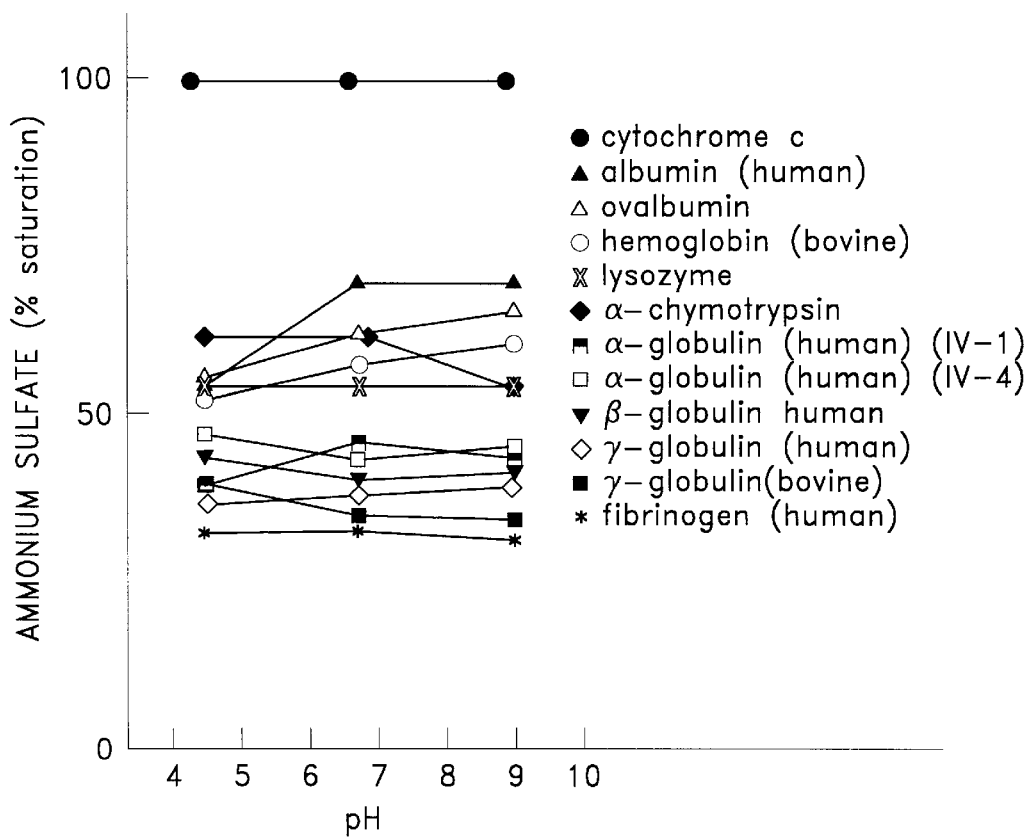
FIG. 21 is a graph illustrating the precipitation points of several stable proteins as a function of pH.

The data shown in FIG. 21 indicates that the fractionation methods described above may be especially useful for the separation of monoclonal antibody from a hybridoma supernatant containing a significant amount of albumin and low molecular weight compounds. A specific example of such a separation is provided by Example 3 above. Furthermore, data of FIG. 21 indicates that such a separation may be improved by performing the protocol at a basic pH.

In contrast, if the raw sample is a cell lysate containing many species of protein with intermediate precipitation values of, for example, 40% to 55%, a one step separation protocol may not be particularly effective. In these cases, a specific binding ligand which attaches to the target protein to modify its precipitation characteristics will likely improve the fractionation. A specific example of this situation is provided by Example 6 above.

The invention thus provides distinct advantages in terms of labor savings and purification efficiency. Effluent is monitored continuously as in liquid chromatography and the entire process can be automated. Very small samples may be purified in small capacity channels and collected in a concentrated state. Furthermore, the process may be easily scaled up for industrial use in the production of drugs, diagnostic assays, reagents, and other pharmaceutical products. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A protein fractionation apparatus comprising:
   a source of precipitating salt;
   a first channel coupled to said source such that the concentration of precipitating salt in said channel varies substantially continuously along the length of said channel; and
   a protein detector coupled to an output of said first channel.

2. The apparatus of claim 1, wherein said channel is spiral or helical.

3. The apparatus of claim 1, wherein the concentration of said precipitating salt increases substantially continuously from a first end of said channel to a second end of said channel.

4. The apparatus of claim 1, wherein the concentration of said precipitating salt varies approximately according to the formula $C(1-e^{-kx})$, wherein C and k are constants, and wherein x is the distance from said first end of said channel.

5. The apparatus of claim 1, wherein the concentration of said precipitating salt varies approximately according to the formula $Ce^{-kx}$, wherein C and k are constants, and wherein x is the distance from said first end of said channel.

6. The apparatus of claim 1, wherein the concentration of said precipitating salt at one or more positions along said channel varies with time.

7. The apparatus of claim 1, wherein said source is coupled to a second channel containing a saturated solution of said precipitating salt, and wherein said first channel is coupled to said second channel through a semi-permeable membrane.

8. A fractionation apparatus comprising:
   a first channel comprising a solution containing a substance selected from the group consisting of precipitating salt, organic solvent, acid, base, and polymer and coupled to a source there of, wherein the concentration of said substance in said first channel is approximately constant with position along said first channel;
   a second channel coupled to said first channel through a semi-permeable membrane, so as to receive a portion of said substance, whereby said second channel has therein a solution of said substance in which the concentration of said substance in said second channel arises from diffusion of said substance through the membrane, wherein the concentration of said substance in said second channel is substantially different at a first position in said second channel than at a second position in said second channel; and a gradient pump configured to produce a timewise reduction in concentration of said substance throughout said second channel.

9. The apparatus of claim 8, wherein said first channel and second channel are spiral or helical.

10. The apparatus of claim 8, wherein the concentration of said substance in said second channel varies with time.

11. The apparatus of claim 8, wherein said solution of substance in said first channel flows in a direction opposite to a direction of flow of said substance in said second channel such that the concentration of substance in said second channel varies approximately according to the formula $C(1-e^{-kx})$, wherein C and k are constants, and wherein x is the distance from an end of said second channel.

12. The apparatus of claim 11, wherein a flow rate of said solution in said first channel is higher than a flow rate of said solution in said second channel.

13. The apparatus of claim 11, wherein the concentration of said substance in said first channel decreases approximately linearly with time.

14. A fractionation apparatus comprising:

a first channel containing a sample for fractionation;

a second channel containing a substantially saturated solution of a precipitating salt and coupled to a soure of said salt; and a semi-permeable membrane separating said first channel from said second channel.

15. The apparatus of claim 14, wherein said first channel and said second channel are spiral or helical.

16. The apparatus of claim 15, wherein said first and said second channels each comprise a spiral groove in a surface of a plastic disk.

17. The apparatus of claim 14, comprising a tube of semi-permeable material surrounded by a second tube, whereby said second channel comprises an interior region of said semi-permeable tube and said first channel comprises a region between said semi-permeable tube and said second tube.

18. A method of sample fractionation comprising:

varying a concentration of a precipitation reagent from a first end of a channel to a second end of a channel;

introducing a sample into said first end of said channel; and eluting said sample from said second end of said channel by reducing the concentration of said precipitation reagent throughout said channel.

19. The method of claim 18, wherein said concentration of said precipitation reagent is lower in a region of said channel proximate to said first end of said channel than said concentration in a region of said channel proximate to said second end of said channel.

20. The method of claim 18, wherein said concentration of said precipitation reagent is higher in a region of said channel proximate to said first end of said channel than said concentration in a region of said channel proximate to said second end of said channel.

21. The method of claim 18, additionally comprising increasing the concentration of said precipitation reagent throughout said channel during the process of eluting said sample.

22. A fractionation apparatus comprising a source of precipitating salt:

a sample flow channel coupled to said source;

means for forming a continuously spatially increasing precipitating salt concentration from a first portion of said channel to a second portion of said channel so as to selectively precipitate a plurality of different chemical species at different locations of said channel; and means for producing a timewise reduction in precipitating salt concentration throughout said channel so as to elute at least some of said plurality of different chemical species from said channel at different times.

23. The apparatus of claim 22, additionally comprising a fraction detector at an end of said channel.

24. A method of separating molecules having one or more different properties comprising:

introducing a substantially saturated solution of precipitating salt into a first flow channel;

introducing a sample into a second flow channel which is separated from said first flow channel by a semi-permeable membrane.

25. The method of claim 24, wherein said precipitation reagent comprises ammonium sulfate.

26. The method of claim 24, wherein a fluid flow rate through said first channel is much greater than a fluid flow rate through said second channel.

27. The method of claim 24, wherein fluid flow through said first channel is in the opposite direction of fluid flow through said second channel.

28. The method of claim 24, wherein introducing said solution of precipitating salt comprises introducing a timewise decreasing concentration of precipitating salt into said first flow channel.

* * * * *

UNITED STATES PATENT AND TRADEMARK OFFICE
CERTIFICATE OF CORRECTION

PATENT NO.     : 6,379,973 B1                                            Page 1 of 1
DATED          : April 30, 2002
INVENTOR(S)    : Yoichiro Ito It is certified that error appears in the above-identified patent and that said Letters Patent is hereby corrected as shown below:

<u>Title page,</u>
Item [75], should read:
-- Inventor:    Yoichiro Ito, Bethesda, MD (US) --

Signed and Sealed this

Twenty-fifth Day of June, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,379,973 B1
DATED : April 30, 2002
INVENTOR(S) : Yoichiro Ito

It is certified that error appears in the above-identified patent and that said Letters Patent is hereby corrected as shown below:

<u>Column 17,</u>
Line 31, please delete "soure" and insert therefore, -- source --

Signed and Sealed this

Eighth Day of April, 2003

JAMES E. ROGAN
*Director of the United States Patent and Trademark Office*